United States Patent
Discenzo

(10) Patent No.: US 7,516,650 B2
(45) Date of Patent: Apr. 14, 2009

(54) LUBRICITY MEASUREMENT USING MEMS SENSOR

(75) Inventor: Frederick M. Discenzo, Brecksville, OH (US)

(73) Assignee: Rockwell Automation Technologies, Inc., Mayfield Heights, OH (US)

(*) Notice: Subject to any disclaimer, the term of this patent is extended or adjusted under 35 U.S.C. 154(b) by 64 days.

(21) Appl. No.: 11/761,196

(22) Filed: Jun. 11, 2007

(65) Prior Publication Data

US 2007/0245811 A1    Oct. 25, 2007

Related U.S. Application Data

(62) Division of application No. 11/297,267, filed on Dec. 8, 2005, now Pat. No. 7,228,727, which is a division of application No. 10/675,846, filed on Sep. 30, 2003, now Pat. No. 7,024,920.

(51) Int. Cl.
*G01N 33/30* (2006.01)
*G01N 11/00* (2006.01)

(52) U.S. Cl. .............. 73/53.01; 73/53.06; 73/61.41; 702/50

(58) Field of Classification Search ............ 73/10, 73/53.05, 53.06, 54.01, 54.02, 54.22, 54.23, 73/54.28, 54.37, 54.39, 61.41, 61.42; 702/50
See application file for complete search history.

(56) References Cited

U.S. PATENT DOCUMENTS

| | | | |
|---|---|---|---|
| 3,823,599 A * | 7/1974 | Litz et al. .................. 73/10 |
| 5,338,442 A | 8/1994 | Siskin et al. | |
| 5,640,103 A | 6/1997 | Petsche et al. | |
| 5,674,401 A | 10/1997 | Dickert et al. | |
| 5,817,928 A | 10/1998 | Garvey et al. | |
| 5,957,170 A | 9/1999 | Bedi et al. | |
| 5,959,189 A | 9/1999 | Jeng et al. | |
| 5,964,318 A | 10/1999 | Boyle et al. | |
| 5,968,371 A | 10/1999 | Verdegan et al. | |
| 5,969,227 A | 10/1999 | Kenney | |
| 6,023,961 A | 2/2000 | Discenzo et al. | |
| 6,070,456 A * | 6/2000 | Cameron et al. .......... 73/53.05 |
| 6,105,415 A * | 8/2000 | Kenney .................. 73/10 |
| 6,167,709 B1 | 1/2001 | Caracciolo et al. | |
| 6,196,057 B1 | 3/2001 | Discenzo | |
| 6,286,363 B1 | 9/2001 | Discenzo | |
| 6,324,899 B1 | 12/2001 | Discenzo | |
| 6,434,512 B1 | 8/2002 | Discenzo | |
| 6,534,010 B2 | 3/2003 | Sentmanat | |
| 6,561,010 B2 | 5/2003 | Wilson et al. | |
| 6,805,312 B2 | 10/2004 | Capp | |
| 6,823,718 B2 * | 11/2004 | Sandford et al. .............. 73/37 |

(Continued)

OTHER PUBLICATIONS

Stuebner, Partial European Search Report EP 04 02 3004. Munich, Jan. 7, 2005.

*Primary Examiner*—Daniel S Larkin
(74) *Attorney, Agent, or Firm*—Amin Turocy & Calvin LLP; R. Scott Speroff

(57) ABSTRACT

A system that facilitates in situ determination of lubricity in a fluid comprises a multi-element sensor positioned within a machine, wherein the multi-element sensor obtains data regarding a plurality of parameters of a fluid. A component calculates lubricity of the fluid based at least in part upon the measured parameters.

18 Claims, 26 Drawing Sheets

U.S. PATENT DOCUMENTS

| | | |
|---|---|---|
| 6,922,664 B1 | 7/2005 | Fernandez et al. |
| 6,994,016 B1 | 2/2006 | Bunker et al. |
| 7,019,638 B1 | 3/2006 | Wallace |
| 7,024,920 B2 | 4/2006 | Discenzo |
| 2003/0101801 A1 | 6/2003 | Wilson et al. |
| 2004/0052702 A1 | 3/2004 | Shuman et al. |
| 2005/0068846 A1 | 3/2005 | Wulf et al. |
| 2005/0107980 A1 | 5/2005 | Cocchis et al. |
| 2005/0112255 A1 | 5/2005 | Tottenham et al. |
| 2005/0198990 A1 | 9/2005 | Kateman et al. |
| 2005/0256774 A1 | 11/2005 | Clothier et al. |
| 2007/0211784 A1 | 9/2007 | Simunovic et al. |

* cited by examiner

LUBRICITY MEASUREMENT USING MEMS SENSOR

CROSS-REFERENCE TO RELATED APPLICATIONS

This application is a Divisional of U.S. patent application Ser. No. 11/297,267, filed Dec. 8, 2005, now U.S. Pat. No. 7,228,727, and entitled LUBRICITY MEASUREMENT USING MEMS SENSOR, which is a Divisional of U.S. patent application Ser. No. 10/675,846, filed Sep. 30, 2003, now U.S. Pat. No. 7,024,920, and entitled LUBRICITY MEASUREMENT USING MEMS SENSOR, the entirety of which is incorporated herein by reference.

TECHNICAL FIELD

The present invention generally relates to measurement and analysis of multiple parameters of fluids utilized in machinery. More particularly, the invention relates to a system and/or methodology that facilitates continuous in situ measurement and analysis of lubricity of a fluid.

BACKGROUND OF THE INVENTION

Dynamoelectric machines, such as motors and generators and other rotating machines, such as gears and bearing systems, are widely employed in industrial and commercial facilities. These machines are relied upon to operate with minimal attention and provide for long, reliable operation. Many facilities operate several hundred or even thousands of such machines concurrently, several of which are integrated into a large interdependent process or system. Like most machinery, at least a small percentage of such equipment is prone to failure. Some of these failures can be attributed to loss of lubrication, incorrect lubrication, lubrication breakdown, or lubrication contamination.

Depending on the application, failure of a machine in service can possibly lead to system or process latency, inconvenience, material scrap, machinery damage, hazardous material cleanup, and even a dangerous situation. Thus, it is desirable to diagnose machinery for possible failure or faults early in order to take preventive action and avoid such problems. Absent special monitoring for certain lubrication problems, a problem may have an insidious effect in that although only a minor problem on the outset, the problem could become serious if not detected. For example, bearing problems due to inadequate lubrication, lubrication contamination or other causes may not become apparent until significant damage has occurred.

Proper lubrication facilitates extension of machinery life. For example, when motor lubricant is continuously exposed to high temperatures, high speeds, stress or loads, and an oxidizing environment, the lubricant will deteriorate and lose its lubricating effectiveness. The loss of lubricating effectiveness will affect two main functions of a lubrication system, namely: (1) to reduce friction; and (2) to remove heat. Continued operation of such a degraded system may result in even greater heat generation and accelerated system degradation eventually leading to substantial machinery damage and ultimately catastrophic failure. To protect the motor, the lubricant should be changed in a timely fashion. However, a balance must be struck—on one hand it is undesirable to replace an adequate lubricant but on the other hand it is desired to replace a lubricant that is in its initial stages of breakdown or contamination prior to occurrence of equipment damage. As each particular application of a lubricant is relatively unique with respect to when the lubricant will breakdown or possibly become contaminated, it becomes necessary to monitor the lubricant.

Lubricity can be defined as "an ability of a lubricant to reduce friction between moving, loaded surfaces." Prior to a mandated reduction in the sulfur content of diesel fuels in the early 90's, no acceptable measurement of lubricity of a fluid was defined. Reduction of sulfur in diesel fuels typically is accomplished via hydro heating, which inadvertently removes lubricating elements from the fuels. Such reduction of sulfur (and thus lubricating elements) has caused premature equipment breakdowns and, in some cases, catastrophic failure. Thus, a demand arose for a system and/or methodology for testing for lubricity of a fluid. Laboratory procedures and measures of lubricity were defined and incorporated into ASTM standards. Such procedures include the Standard Test Method for Evaluating Lubricity of Diesel Fuels by the Scuffing Load Ball-on-Cylinder Lubricity Evaluator (SLBOCLE), the Test Method for Evaluating Diesel Fuel Lubricity by an Injection Pump Rig, the Standard Test Method for Evaluating Lubricity of Diesel Fuels by the High-Frequency Reciprocating Rig (HFRR), and other laboratory testing procedures.

Unfortunately, performing the testing methods described above requires expensive, bulky equipment. Furthermore, the ASTM testing methods require a substantial amount of time for completion, and moreover require operator intervention. More importantly, these tests must be done off-line in a laboratory or bench-top setting. They cannot be done on-line, in real time as the machinery operates. It is to be understood, however, that no standard of lubricity presently exists—only disparate procedures for testing lubricity. The measurements obtained via employing the ASTM testing methods are error-prone due to complexity of such testing procedures, and reproducing the measurements for verification purposes is difficult due to an amount of time required for obtaining a measurement. Moreover, the laboratory testing procedures do not account for an environment in which a lubricant will be employed. For instance, surface coating of metallic parts within a machine can impact an ability of a lubricant to effectively mitigate wear between two moving components. Also, a fluid's ability to carry particular particles within an operating environment can impact lubricity of the fluid. With a continuing trend towards limiting the amount of sulfur present in fuels and lubricants, an in situ sensor that continuously monitors lubricity of a fluid can mitigate breakdown and catastrophic failure of machinery.

In view of at least the above, there exists a strong need in the art for a system and/or methodology facilitating continuous in situ measurement and analysis of parameters relating to fluid lubricity, and a system and/or methodology for maintaining such fluids.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention facilitates in situ attainment of a measurement of lubricity of a fluid as well as attainment of a Fourier Transform Infra Red spectrum plot. The present invention is a significant improvement over conventional systems and/or methods for determining lubricity of a fluid in that an inexpensive multi-element sensor can be employed to obtain data necessary to calculate lubricity. Moreover, the multi-element sensor can be extremely small, thereby allowing placement of the sensor in positions within machinery that lubricity is extremely important to proper operation of the machinery (e.g., fuel pumps, bearing raceways, . . . ). Furthermore, the present invention facilitates continuous monitoring of various parameters of a fluid, and thus facilitates continuous monitoring of lubricity, as lubricity is calculated based at least in part upon data obtained from the multi-element sensor. After a measurement relating to automatically maintaining fluid as well as automatically controlling operation of a machine. For example, if fluid displays insufficient lubricity, additives that enhance lubricity can be added to the fluid. Moreover, the speed of operation of a machine can be accelerated or slowed based upon obtained values of lubricity.

Multi-elements sensor(s) are employed to obtain data regarding a plurality of parameters of a fluid utilized in machinery. Such parameters can include but are not limited to temperature, pH, viscosity, density, oxidation, TAN, presence of water, presence of ZDDP and/or TCP, conductance, etc. The data can thereafter be received by a component that facilitates filtering and/or fusion of such data. The component can utilize models based on laboratory test procedures employed to measure lubricity of various fluids. More particularly, the component can include a first-order chemical model and pattern recognition algorithms that correlate sensor readings with laboratory lubricity measurements.

In accordance with one aspect of the present invention, MEMs viscosity sensors can be employed in connection with determining lubricity of a fluid. Finger-like elements of the viscosity sensors can be coated on surfaces moving in close proximity with disparate surfaces. A voltage source can cause the finger-like elements to vibrate, and upon backing out the voltage data is obtained regarding an ability of a fluid to adhere to the disparate surfaces. Such ability to adhere (or "stickiness") is relevant to lubricity of the fluid. Furthermore, the finger-like elements of the viscosity sensors can be disparately spaced, thereby leaving larger gaps between finger-like elements in a particular viscosity sensor compared to a differing viscosity sensor. Voltages can then be applied to the viscosity sensors causing the finger-like elements of the viscosity sensors to vibrate. Upon backing out the voltage, comparative measurements pertaining to an ability of the fluid to adhere to disparately spaced finger-like elements can be employed in connection with robustly calculating lubricity.

In accordance with another important aspect of the present invention, several non-traditional sensing elements can be provided on the multi-element sensor. For instance, two surfaces can be provided forces that require such two surfaces to contact one another. The forces will be applied to require generation of a frictional force between the two surfaces. Monitoring forces utilized to generate the frictional force and relative displacement between the two surfaces enables additional data relevant to lubricity of the fluid to be obtained.

To the accomplishment of the foregoing and related ends, the invention then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

DETAILED DESCRIPTION OF THE INVENTION

Figure 1:
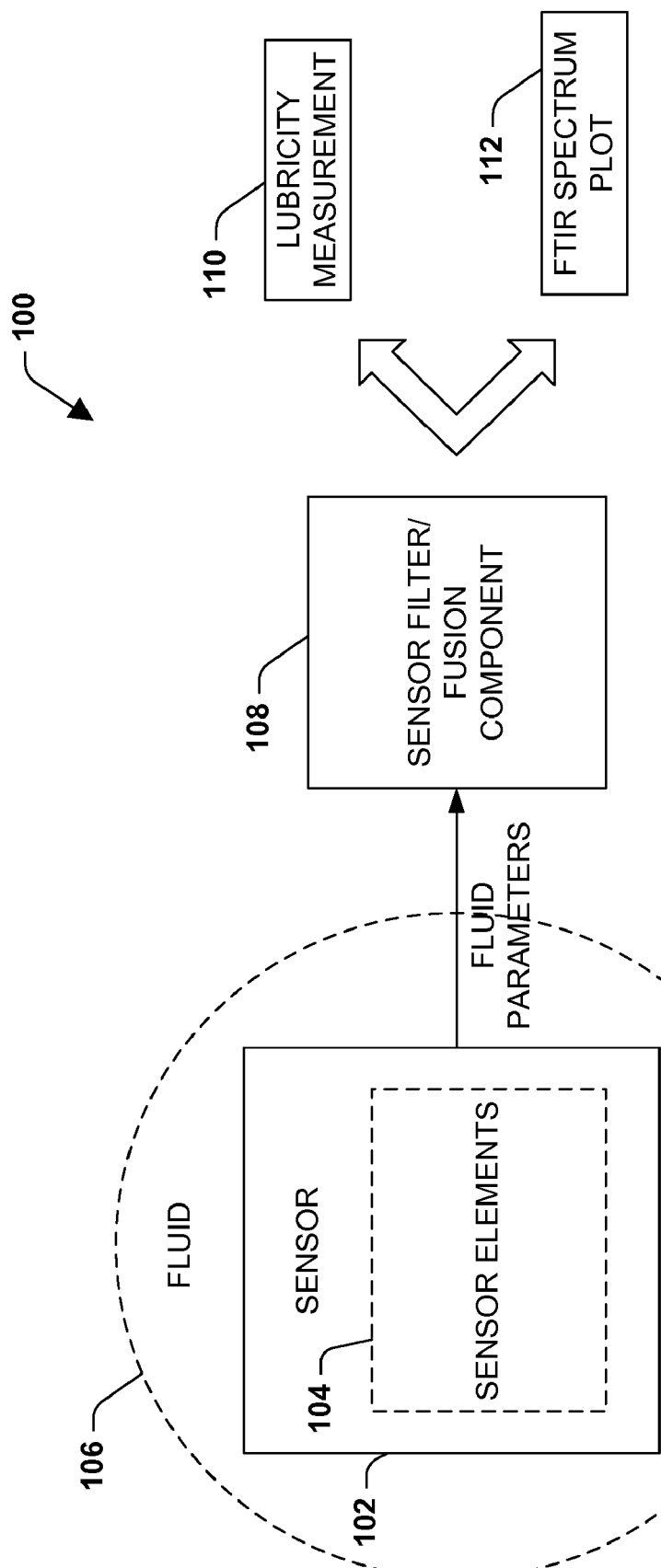
FIG. 1 is a block diagram of a system that facilitates calculation of lubricity of a fluid within machinery in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the term "computer component" is intended to refer to a computer-related entity, either hardware, a combination of hardware and software, software, or software in execution. For example, a computer component may be, but is not limited to being, a process running on a processor, a processor, an object, an executable, a thread of execution, a program, and/or a computer. By way of illustration, both an application running on a server and the server can be a computer component. One or more computer components may reside within a process and/or thread of execution and a component may be localized on one computer and/or distributed between two or more computers.

Referring now to the drawings, FIG. 1 illustrates a high-level system overview in connection with one particular aspect of the subject invention. The present invention relates to a novel system 100 for providing continuous in situ indications of lubricity of a fluid within machinery. A model of lubricity can be generated based upon ASTM procedures. For example, the present inventor analyzed various measurements obtained from disparate ASTM tests to provide a robust model of lubricity. The present invention utilizes various parameters that, while not directly measuring lubricity, can indicate lubricity of a fluid in a machine. Furthermore, the parameters can be continuously sensed in situ with sensing components that are much less expensive than equipment required under ASTM standards. The sensing components are also smaller, lighter, operate automatically, operate continuously, operate repeatedly, and require less power than equipment required under ASTM standards. Parameters obtained from the sensing components can thereafter be employed to maintain fluid to contain sufficient lubricity given a particular application. Substantially similar parameters can further be utilized to generate an FTIR spectrum to further analyze the fluid.

The system 100 includes a sensor 102 that includes a plurality of sensor elements 104 employed to obtain measurements of various parameters of a fluid, such as temperature, pH, viscosity, presence or particular additives, electro-chemical activity, TAN, density, dielectric, etc. Furthermore, the sensor elements 104 can include devices specifically designed to determine an index of lubricity. For instance, two surfaces can be provided, wherein actuators or other force-providing devices can provide one or more forces to create friction between the surfaces. An amount of force provided and the relative motion between the surfaces can be one particular measurement that is indicative of lubricity. For another example, an amount of fluid that adheres to a vibrating surface can be another parameter indicative of lubricity.

The sensor 102 is immersed in a fluid 106, and the sensor elements 104 can obtain measurements of parameters relating to the fluid 106 (e.g., temperature, density, ...). The fluid 106 can be in a fluid reservoir, in a flow line within machinery, in a filter, in a pump, in a valve, or within other such structure, component, or material exposed to a fluid. Ideally, the sensor 104 is positioned within machinery where friction of moving parts can result in machine wear and/or breakdown. For instance, the sensor 104 can be positioned in a bearing raceway, a fuel pump, and/or any other suitable position within machinery. The sensor 104 can be extremely small, thereby enabling positioning of the sensor 104 within components of machinery that are typically difficult or impossible to reach by a service engineer. The small size and low cost of the sensor 104 permits embedding multiple sensor devices in a particular machine, enabling determination of lubricity at various location(s) within a machine and in secondary fluid and alternate fluid reservoirs or fluid systems such as a reserve fuel system or secondary hydraulic system in an aircraft. Positioning of the sensor 104 within machinery enables determining lubricity within an operating environment, rather than extracting a sample of the fluid 106 and performing laboratory tests on such fluid 106. This in situ monitoring is beneficial, as an operating environment can affect lubricity of the fluid 106. For instance, surface condition such as surface material and surface charge field can affect lubricity of a fluid. Moreover, an ability of fluid to carry chemical compounds within machinery will also affect the lubricity of the fluid 106.

The parameters of the fluid 106 sensed by the sensor elements 104 can then be received by a sensor filter/fusion component 108, which facilitates generation of a robust lubricity measurement 110 from a plurality of sensed parameters. The sensor filter/fusion component 108 can employ neural networks, Bayesian belief networks, support vector machines, expert systems, fuzzy logic, data fusion engines, fluid models (chemical, fluid transport, tribological, molecular-physics, and stochastic) and other "intelligent" networks or a combination of these techniques to utilize sensed parameters of the fluid 106 to output a lubricity measurement 110. For instance, the sensor filter/fusion component 108 can provide weights to parameters sensed by the sensor elements 104. In particular, the sensor filter/fusion component 108 can allow particular parameters of the fluid 106 to be of greater influence than various other parameters in outputting the lubricity measurement 110 when given that the sensor 102 is at a particular position within machinery and the machinery is at a specific level of operation. Moreover, the sensor filter/fusion component 108 can include a model and pattern recognition algorithms to correlate sensor readings with laboratory lubricity measurements. One particular sensor fusion system and/or methodology that can be employed in connection with the present invention is described in U.S. Pat. No. 6,286,363, entitled INTEGRATED MULTI-ELEMENT LUBRICATION SENSOR AND HEALTH LUBRICANT ASSESSMENT SYSTEM, which as mentioned above is hereby incorporated by reference in its entirety.

In accordance with another aspect of the present invention, the sensor filter/fusion component 108 can infer weighting of parameters of the fluid 106 based at least partly on prior usage and current context of a user and/or machine. As used herein, the term "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification schemes and/or systems (e.g., support vector machines, neural networks, expert systems, Bayesian belief networks, fuzzy logic, case-based reasoning, belief models, data fusion engines . . . ) can be employed in connection with performing automatic and/or inferred action in connection with the subject invention. For example, the sensor filter/fusion component 108 can infer weights to be given to each fluid parameter even when a machine is not in operation based upon prior usage of the machine. Thus, prior to starting and/or restarting the machine an operator can confirm that sufficient lubricity exists for the typical operation of the machine.

In accordance with another aspect of the present invention, the determined lubricity measurement can be employed to control chemicals within the fluid 106 before, during, and/or after machine operation. For instance, the lubricity measurement can be utilized to automatically inject components that provide greater lubricity to a fluid during instances that the lubricity measurement 110 isn't sufficient. As another example, when high fluid stress is sensed and limited lubricity is determined from sensor measurements, a prescribed amount of EP (extreme pressure) additive may be admitted to the system to establish an acceptable level of lubricity. The resultant new value of lubricity is then measured to confirm that the expected change in lubricity has in fact occurred and that the sensing, control, additive reservoir, and other system components are working properly. Furthermore, the obtained lubricity measurement can be employed to confirm that the fluid is capable of meeting severe loads, and that fluid lifetime and machinery lifetime has been extended. Moreover, an ability to provide a continuous measurement of lubricity in connection with controlling lubricity of the fluid 106 ensures that catastrophic breakdown of machinery will not occur due to lack of lubricity.

The sensor filter/fusion component 108 can also be utilized in connection with the sensor elements 104 to synthesize a Fourier Transform Infra-Red (FTIR) spectrum plot 112. Particular compounds and contaminants in the fluid 106 that are sensed utilizing laboratory techniques such as FTIR spectroscopy also affect sensor readings for a plurality of parameters of the fluid 106 (e.g., pH, water, TAN, chemical contaminants, fuel . . . ). For example, the presence and amount of water in the fluid 106 will generate a characteristic alteration in a cyclic voltammetry curve and dialectric reading of the sensor elements 104. Similarly, presence and amount of water also exhibit a characteristic alteration in amplitude of the FTIR spectrum plot 112 at a particular wavenumber. For example, the presence of $H_2O$ in a sample will exhibit a peak at wavenumbers 3450-3330 $cm^{-1}$ and carbonyl compounds (e.g. oxidized compounds) will exhibit a peak at wavenumbers 1755-1695 $cm^{-1}$. Such parameters can be sensed in situ by the sensor 102 via utilizing the sensor elements 104. The multiple sensor elements 104, which can include a dielectric sensor, TAN sensor, electro-chemical sensor, etc. can detect particular chemicals that exhibit a change in the FTIR spectrum. For example, the I-V (current-voltage) curve generated by performing cyclic-voltammetry with an electro-chemical sensor element exhibits unique characteristics for water and other contaminants. These same chemicals exhibit a characteristic pattern in the FTIR plot. As FTIR spectrum information is embedded (or encoded) in sensor readings of the sensor elements 104, the FTIR spectrum plot 112 can be obtained via employing the sensor filter/fusion component 108.

For example, artificial neural networks have been demonstrated as effective algorithms for extracting encoded information from one data series and synthesizing a new, derived series originally embedded in the original data series. Artificial neural networks can be used by providing multiple sensor readings from the sensor elements 104 to a pre-processing function. The pre-processing function can perform any needed scaling, filtering, signal processing, and computations to combine or calculate additional parameters. An array of values from the pre-processing function (resulting from a manipulation of sensor readings from the sensor element 104) can be provided as input to the artificial neural network. The neural network can be a wide range of established neural net architectures. An exemplary network is a feed-forward neural network with back-propagation training. The feed-forward network is previously trained with a suite of data exemplars comprised of readings from the sensor elements 104 and corresponding FTIR spectrum data values. These training values are extracted from a range of fluids including good fluid, degraded fluid, and contaminated fluid such as will be expected to be experienced during sensor operation. Other well-known systems and/or methods may be used to synthesize the FTIR spectrum, such as algorithmic methods employing curve fitting, expert systems, stochastic models, fuzzy logic, data fusion engines, Bayesian belief networks, and support vector machines.

An important characteristic of the sensor 102 comprising a plurality of sensing elements 104 is that several of the individual sensor elements 104 are not merely passive devices providing a specific sampled electrical value. Rather, the sensor elements 104 can be actively stimulated in a manner that will provide for a more accurate and a broader range of information regarding condition of the fluid 106 and contaminants present within the fluid 106. For example, disparate stimulus frequencies and amplitudes can indicate different fluid properties and contaminants.

For example, electrochemical sensor electrodes can be provided with either a triangular wave or sinusoidal waveform of a particular voltage value and frequency. The voltage value and frequency applied to the electrochemical sensor will indicate the presence of particular compounds, additives, and contaminants such as water. Spanning particular voltage ranges and frequencies will cause certain compounds to oxidize and reduce thereby providing an indication in the IV (current-voltage) curve of the presence of these different chemicals. The selection of voltage and frequency ranges can be dynamically adjusted to focus in on compounds of interest or to provide a more complete FTIR spectrum to be synthesized. For example, existence of a particular compound of interested can be indicated on a general wide voltage sweep IV curve. Based on the interpreted IV curve, the cyclic voltammetry process can then be repeated with within a very limited voltage range and at a slower frequency to highlight specific contaminants detected. This more precise information can be used to dynamically increase the accuracy and resolution of the synthesized FTIR spectrum as needed.

Similarly, a conductivity sensor element can also be stimulated during operation. Different stimulus frequencies used to activate the conductivity sensor can indicate different fluid properties. For instance, the conductivity sensor element can be stimulated with a 2 kHz sine wave. The resultant signal will indicate a degree of fluid conductivity. A higher frequency stimulus can indicate water presence, and a still higher frequency can indicate fluid capacitance. Disparate fluid properties determined are related to the specific compounds present in the fluid and are reflected in the FTIR spectrum. Other sensor stimulus signals can be dynamically changed or prescribed in real time based on previous sensor responses to provide for a very accurate and robust FTIR spectrum. New compounds that appear in the synthesized FTIR spectrum can be further investigated with targeted, compound-specific stimulus defined for multiple sensor elements (e.g. TAN, Electrochemical, dielectric, MEMs viscosity, . . . ). The broad range of fluid parameters obtained at various prescribed voltages and frequencies can be combined using sensor fusion and synthesis techniques to generate a synthetic FTIR spectrum. After the FTIR spectrum plot 112 is synthesized from parameters sensed by the sensor elements 104, the spectrum plot 112 can be analyzed by established analytical methods. A significant body of knowledge exists for interpreting the FTIR spectrum plot, which can be readily applied to interpret the new, synthesized FTIR spectrum plot. In a similar manner, since the sensor elements 104 provide information on the chemical composition of the sampled fluid 106, lubricity information is embedded in readings obtained by the sensor elements 104. For example, lubricity enhancing additives, water dilution, fuel dilution, and viscosity may be readily detected by sensor elements 104, and such parameters relate to lubricity performance. It is possible to synthesize lubricity information from values obtained by the sensor elements 104. For example, an artificial neural network as described above may be trained to generate the lubricity value. Other well-known methods can be used to synthesize the lubricity information such as algorithmic methods employing curve fitting, expert systems, stochastic models, fuzzy logic, data fusion engines, Bayesian belief networks, and support vector machines.

In particular, the lubricity measurement 110 and information obtained from analysis of the FTIR spectrum plot 112 can be employed to determine faults or deficiencies in the fluid and automatically alter the chemistry to maintain the fluid 106. For example, operation of a machine and/or alteration of chemical properties of the fluid 106 can be undertaken automatically based at least in part upon the lubricity measurement 110 and the FTIR spectrum plot 112.

Figure 2:
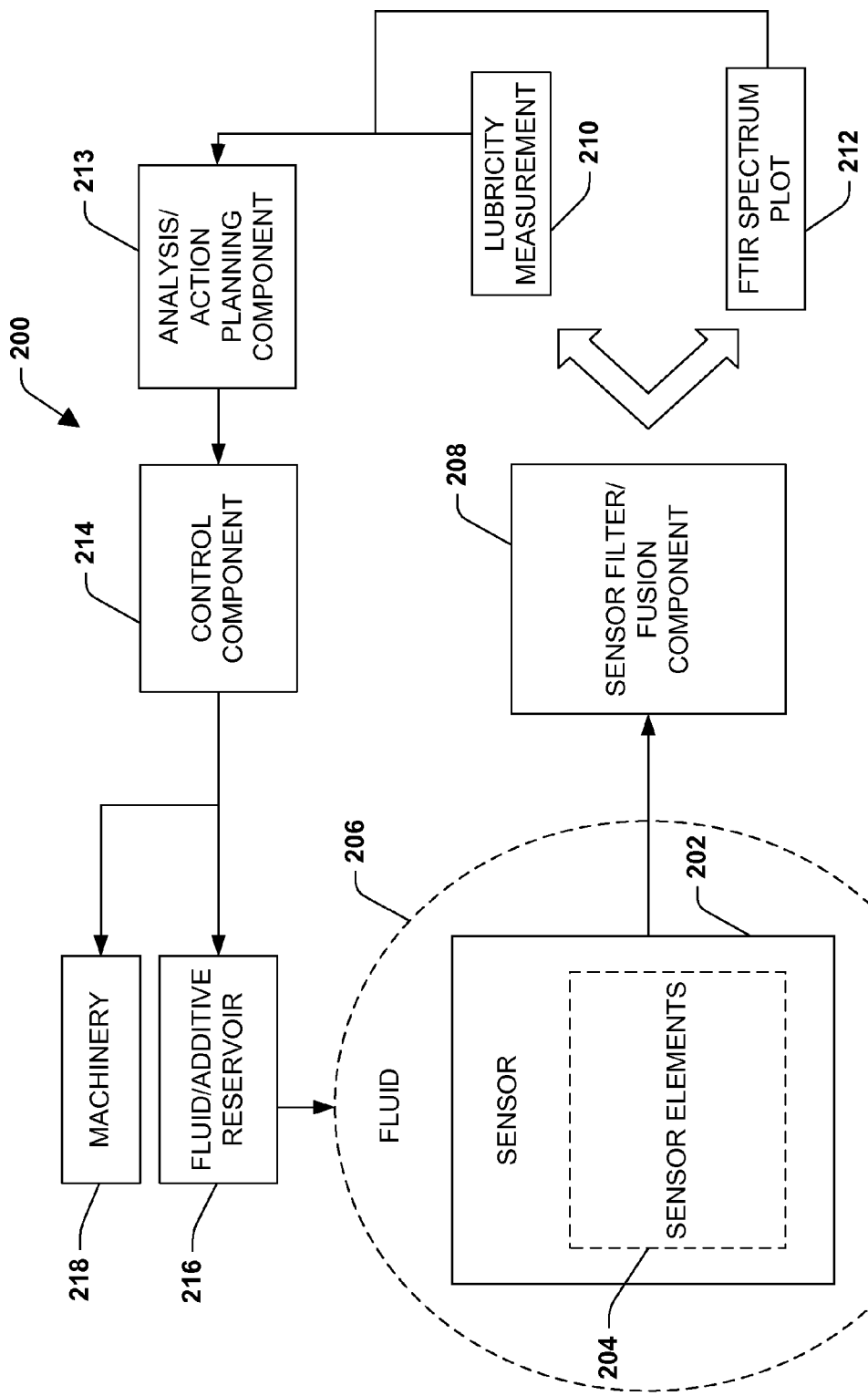
FIG. 2 is a block diagram of a system that facilitates automatic maintenance of a fluid and automatic control of machinery based upon a calculation of lubricity in accordance with an aspect of the present invention.

Turning now to FIG. 2, a system 200 that automatically maintains fluid within machinery based at least in part on a lubricity measurement and/or FTIR spectrum plot is illustrated. The system 200 includes a sensor 202 that comprises a plurality if sensor elements 204 that facilitate measuring particular parameters of a fluid 206. For example, the sensor elements 204 can obtain measurements regarding pH, viscosity, temperature, TAN, conductivity, water content, and various other physical and chemical parameters relating to the fluid 206. Furthermore, the sensor elements 204 can include devices fabricated to particularly obtain data relating to lubricity of the fluid 206 in particular situations. For instance, two surfaces can be positioned to incidentally move relative to one another within the fluid 206, thereby causing friction between the surfaces (e.g., the fluid 206 is provided to reduce friction between the surfaces). An amount of energy provided to the surfaces and distances that the surfaces traveled with respect to one another can be measured and is indicative of lubricity of the fluid 206. A sensor filter/fusion component 208 can receive parameters sensed by the sensor elements 204, and can manipulate such parameters to determine a lubricity measurement 210. The sensor filter/fusion component 208 can, for example, comprise various algorithms that include a first-order chemical model and pattern-recognition algorithms to correlate sensor readings from the sensor elements 204 with laboratory lubricity measurements. Furthermore, as FTIR spectrum information is embedded in readings obtained by the sensor elements 204, the sensor filter/fusion component 208 can facilitate generation of a FTIR spectrum plot 212. The spectrum plot 212 can thereafter be analyzed via conventional methods. For example, the FTIR spectrum may indicate a strong presence of water and oxidative compounds.

An analysis/action planning component 213 can be provided in connection with a control component 214 to facilitate automatic maintenance of the fluid 206 within machinery. For example, the analysis and action planning component 213 can establish a current usefulness of the fluid 206 and identify any deficiencies. The analysis/action planning component 213 will evaluate potential action possible such as injecting new fluid, an anti-oxidant additive, or a lubricity-enhancing additive. The analysis/action planning component 213 may then prescribe a specific amount of additive to be introduced into the fluid supply. Subsequent analysis of the lubricity measurements and FTIR spectrum plot generated will confirm that the fluid change was made and that the desired change in fluid property was achieved. If necessary, additional fluid adjustments can be made in a dynamic, continuous manner.

After the desired fluid change is defined by the analysis and action planning component 213, the control component 214 can facilitate automatic injection of additional fluid and/or fluid additives from a fluid/additive reservoir 216 to the fluid 206. Moreover, the lubricity measurement 210 and the FTIR spectrum plot 212 can be employed as feed-back and/or feed-forward data. The control component 214, for example, can deliver control commands to the fluid/additive reservoir 216 based at least in part upon the lubricity measurement 210 and/or the spectrum plot 212. The fluid/additive reservoir 216 can comprise various actuators, MEMS valves and/or microfluidics that are responsive to the control component 214 (e.g., valves releasing fluid and/or additives into machinery can be responsive to control commands from the control component 214). In accordance with another aspect of the present invention, machinery 218 can be controlled by the control component 214 based at least in part upon the lubricity measurement 210 and/or the FTIR spectrum plot 212. For example, if the lubricity measurement 210 indicates that there is insufficient lubricity for a present and/or future operation of the machinery 218, then the control component 214 can inform the machinery 218 to halt operations or to operate at a level where a lower level of lubricity will not damage the machinery 218.

Figure 3:
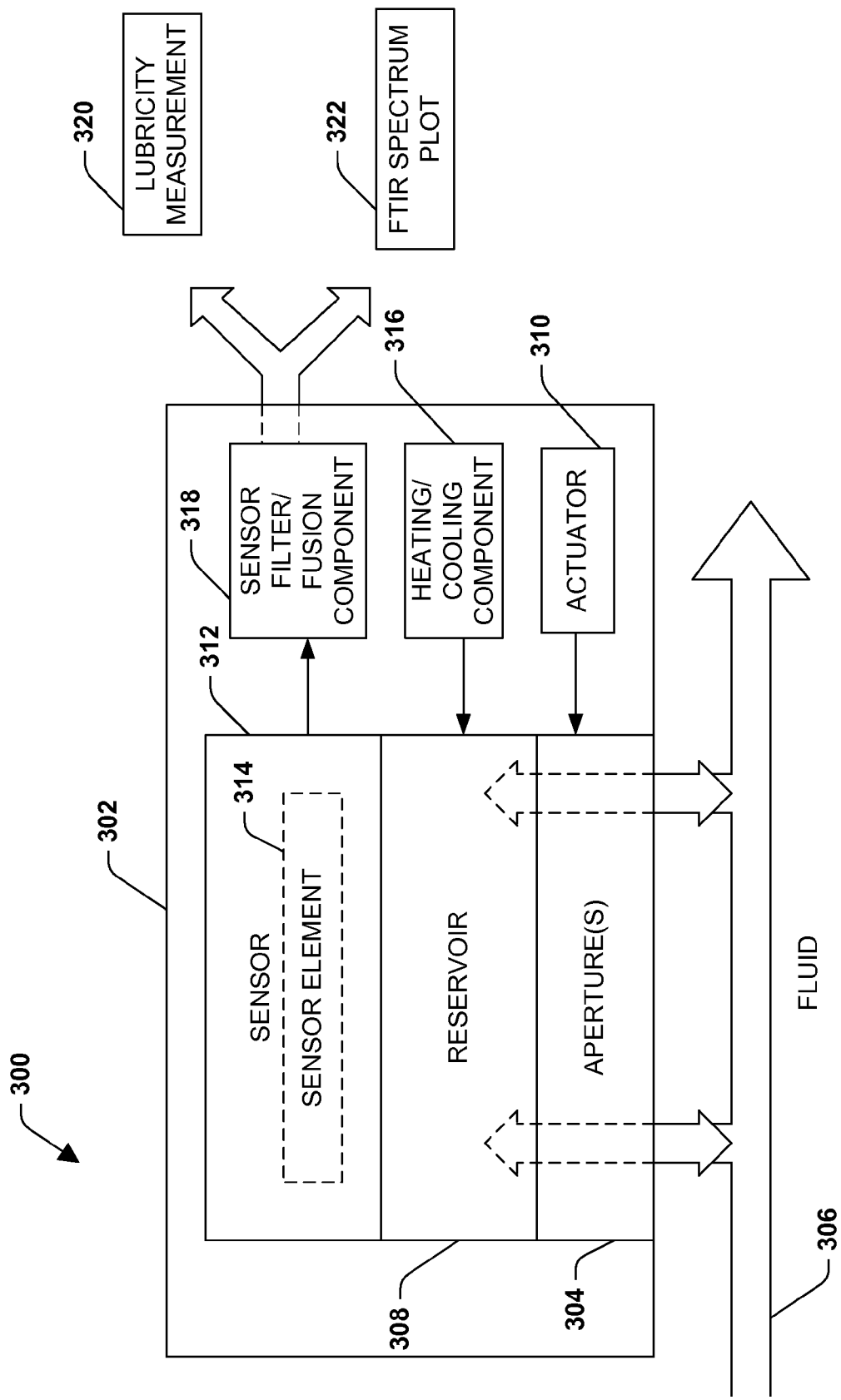
FIG. 3 is a block diagram of a system that facilitates calculation of lubricity of a fluid within machinery in accordance with an aspect of the present invention

Turning now to FIG. 3, a system 300 that facilitates obtaining a measurement of lubricity within a fluid and/or a spectrum plot of a sample of fluid is illustrated. The system 300 includes a casing 302 that has aperture(s) 304 to allow fluid 306 to enter the casing 302. The aperture(s) 304 can be opened to allow fluid to enter the casing 302 and closed upon the filling of a reservoir 308 within the casing 302. An actuator 310 is provided to facilitate opening and/or closing the aperture(s) 304. A sensor 312 with a plurality of sensor elements 314 is provided within the casing, wherein the fluid 306 confined within the reservoir 308 contacts the sensor elements 314. A heating/cooling component 316 is provided to heat and/or cool fluid 306 that is confined within the casing 302. Heating and/or cooling the fluid 306 enables the sensor elements 314 to obtain more robust measurements regarding the fluid 306. The parameters sensed by the sensing elements 314 are received by a sensor fusion component 318, which can manipulate the data received by the sensor elements 314 to output a lubricity measurement 320 and a FTIR spectrum plot 322.

Utilizing the heating/cooling component 316 to vary temperature of the fluid 306 near the sensor elements 314 provides a more complete and accurate mapping of readings from the sensor elements 314 to the spectrum plot 322. A mapping from discrete sensor readings from the sensor elements 314 is performed within the sensor filter/fusion component 318 via standard non-linear mapping techniques such as artificial neural networks. Such mapping technique has been performed in conventional systems that analyze vibration spectrum data from sampled motor current data. It is further to be appreciated that the lubricity measurement 320 and the FTIR spectrum plot 322 be employed to automatically maintain the fluid 306. For example, chemical additives can be automatically added and/or removed from the fluid 306 based at least in part on the measured lubricity 320 and/or the FTIR spectrum plot 322.

Figure 4:
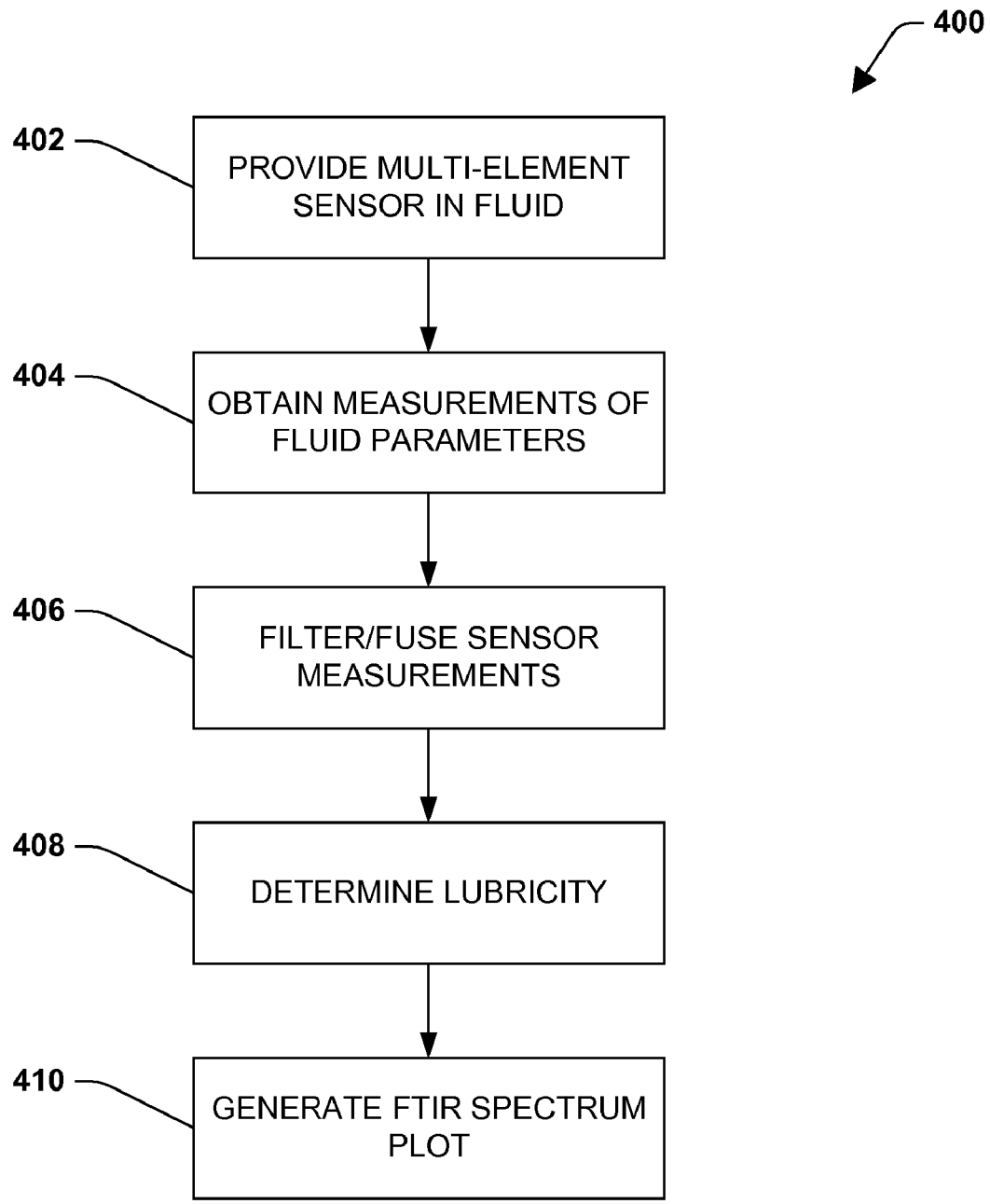
FIG. 4 illustrates a methodology for calculating lubricity in accordance with an aspect of the present invention.

Turning now to FIG. 4, a methodology 400 for determining lubricity of fluid within machinery and obtaining a FTIR spectrum plot of fluid within machinery is described. While, for purposes of simplicity of explanation, the methodology 400 is shown and described as a series of acts, it is to be understood and appreciated that the present invention is not limited by the order of acts, as some acts may, in accordance with the present invention, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

At 402, a multi-element sensor is provided within a fluid. The multi-element sensor can be positioned in machinery in a location that monitoring of lubricity is desirable (e.g., bearing raceway, within a fuel pump, hydraulic reservoir, gearbox, fuel tank, . . . ). The multi-element sensor can sense a plurality of physical and chemical parameters relating to the fluid, including presence of lubricity enhancing additives (e.g., ZDDP and TCP), electrochemistry, TAN, dielectricity, temperature, water, density, viscosity, etc. Furthermore, various other devices that can obtain information indicative of lubricity of the fluid can be provided. For instance, a device with multiple surfaces can be provided, wherein two or more surfaces are forced to contact one another. Moreover, a device that can determine an ability of the fluid to adhere to particular surfaces can be provided.

At 404, the multi-element sensor obtains measurements relating to the fluid (e.g., temperature, density, viscosity, presence of lubricity enhancing additives, ability of the fluid to adhere to particular surfaces, friction measurements, . . . ). At 406 the measurements obtained by the multi-element sensor are filtered and/or fused according to one or more filtering and/or fusing algorithms. In accordance with one aspect of the present invention, the data from the sensor can be filtered and/or fused with respect to a chemical model and pattern recognition correlating to sensor readings with laboratory lubricity measurements. Such a technique ensures that a final lubricity measurement correlates to a measurement that is obtained in laboratory procedures without associated time-consumption and cost. Moreover, as the multi-element sensor can continuously monitor the fluid, a robust control of lubricity can be generated.

At 408, a lubricity measurement is obtained based at least in part upon parameters sensed by the multi-element sensor after filtration/fusion. At 410, a FTIR spectrum plot of the fluid is obtained. Creation of the FTIR spectrum plot is possible due to a correlation that exists between parameters measured by the multi-element sensor and known FTIR spectrum plots. By utilizing sensor filtering and sensor fusion in act 406 together with non-linear sensor mapping, it is possible to construct an FTIR spectrum plot for the particular fluid. The obtained spectrum plot can thereafter be analyzed according to conventional methods.

Figure 5:
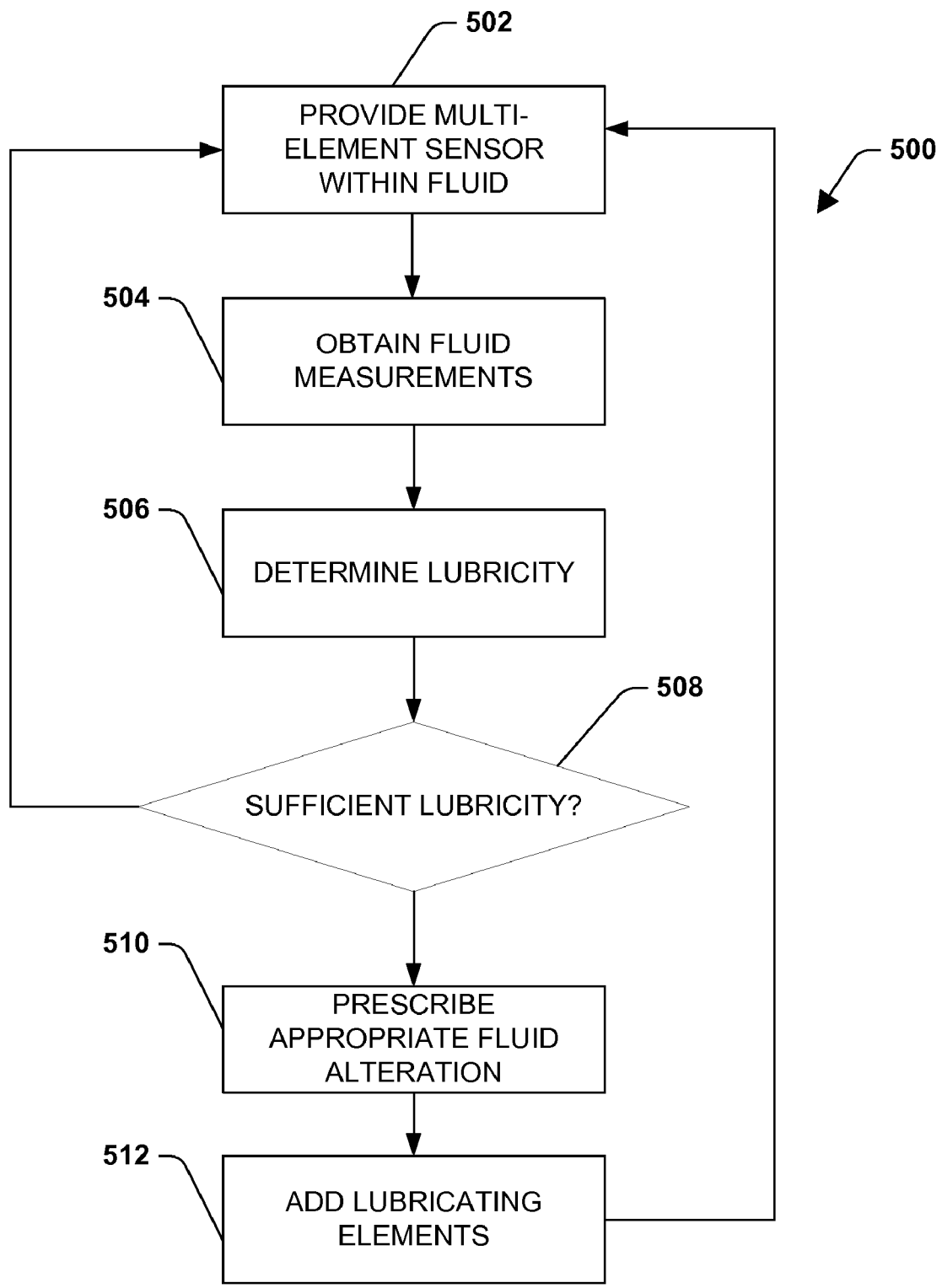
FIG. 5 illustrates a methodology for automatically maintaining a fluid based at least in part upon a calculated lubricity measurement in accordance with an aspect of the present invention.

Turning now to FIG. 5, a method 500 for automatically controlling lubricity within machinery is illustrated. At 502, a multi-element sensor that measures a plurality of parameters relating to a fluid is provided. For instance, the multi-element sensor can obtain measurements related to the fluid physical and chemical properties such as temperature, pH, acidity, water, oxidation levels, etc. Moreover, the multi-element sensor can include friction-sensing elements to facilitate determining lubricity of the fluid. At 504 measurements are obtained by the multi-element sensor. At 506, lubricity of the fluid is determined at least in part via sensor filtering/fusion techniques. At 508 a determination is made regarding whether there is sufficient lubricity within the fluid. If sufficient lubricity exists, the methodology begins again at 502. If not, a prescribed amount of alteration of the fluid is determined at 510. For example, a type of additive and an amount of such additive to inject into the fluid can be determined.

For a more particular example, information such as the amount of stress or loading the fluid is experiencing can facilitate determination of a type and amount of additive to inject into the fluid. A high-temperature, high-vibration environment can place greater demands on the fluid and require a higher degree of lubricity than typically required for cool-running low-stress operation. Based on the context and system demands, a substantial amount of additive to be introduced in the system can be prescribed to provide even greater lubricity and enhance machinery protection. Furthermore, based at least in part upon anticipated future loading and prognostics of expected machinery demands and predicted rate of fluid degradation, additives can be introduced prior to critical fluid parameters (such as lubricity) reaching an unacceptable level. Information regarding future loading and expected degradation rate of fluid can be obtained using established prognostics models such as time-series analysis or artificial neural networks or can be obtained from operational and mission-planning databases. Employing prognostics and taking preventive action before the fluid reaches a critical level provides even greater capability for prolonging fluid life and preventing mechanical damage or catastrophic failure. It is possible that waiting until a parameter value such as lubricity reaches a critical level before initiating control action may make the fluid condition irreversible.

At 512, the prescribed alteration is effectuated into the fluid (e.g., lubricating elements are added). For example, a controller can be provided to constantly receive data relating to lubricity, and automatically maintain the fluid based at least in part upon the received data. The ability to continuously monitor lubricity provides for an enhanced control system and prevents machinery from being subjected to unnecessary friction between moving elements. Thus the ability to continuously monitor lubricity and automatically maintain fluid based at least in part on the measurements is a significant improvement over conventional systems. For example, a conventional system requires extraction of a fluid sample and time-consuming laboratory test procedures to determine lubricity. While the laboratory test procedures are being completed, a machine could be subject to a damaging amount of friction, thereby resulting in irreparable harm to machinery.

In contrast, the present invention enables real-time control of fluid maintenance regarding lubricity of the fluid.

Figure 6:
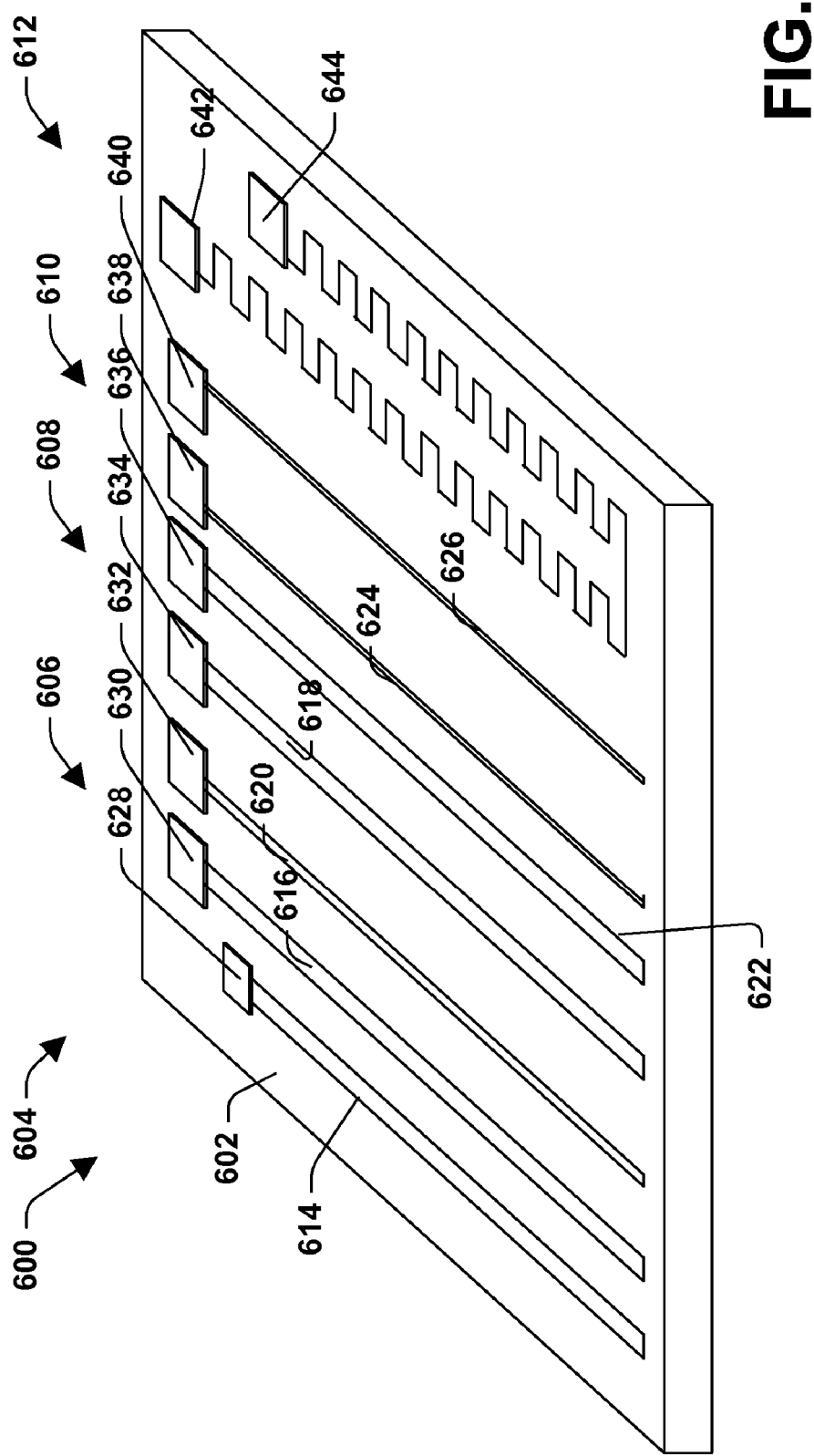
FIG. 6 is an exemplary multi-element sensor that can be utilized in connection with the present invention.

Referring now to FIG. 6, an exemplary micro electromechanical system type (MEMS-type) multi-element fluid sensor 600 that can be employed in connection with determining lubricity of a fluid and generating a FTIR spectrum plot is illustrated. The multi-element fluid sensor 600 affords for continuous in situ monitoring of a variety of fluid parameters via a plurality of sensing devices (elements). A data filtering/fusion framework (not shown) can be associated with the fluid sensor 600 to facilitate condensing, combining, evaluating and interpreting the various sensed data. The sensor 600 can be employed in rotating machinery that utilizes fluid as lubrication. In addition, the sensor 600 can also be applied to measure various parameters of hydraulic fluids and cutting fluids, as well as drilling fluids, fuels, refrigerants, food and cosmetic fluids, and biological fluids. In accordance with one aspect of the present invention, the sensor 600 can be placed within machinery where friction between moving parts can be problematic (e.g., a bearing raceway, fuel pump, valve, . . . ). The fluid sensor 600 includes a semiconductor base 602 that preferably comprises silicon, however, any suitable material may be employed. Located on the surface of the base 602 are a plurality of sensing devices 604 for sensing various parameters of a fluid. More particularly, the sensing devices 604 include a pH or TAN sensor 606 for sensing acidity or basicity of the fluid. A chemical sensor 608 provides for performing electro-chemical operations (e.g. cyclic voltammetry) for sensing chemistry of the fluid. A conductivity sensor 610 provides for sensing electrical conductivity of the fluid. A temperature sensor 612 provides for sensing temperature of the fluid.

The pH/TAN sensor 606 includes a reference electrode 614 comprising any suitable material (e.g., Ag, AgCl) and a pH/TAN electrode 616 comprising any suitable material (e.g., palladium-palladium oxide (Pd-PdO)). The pH/TAN sensor 606 provides for sensing the pH (for aqueous fluids), TAN (total acid number), TBN (total base number), and SAN (strong acid number) of a lubricant or fluid being analyzed. An exemplary discussion relating to pH sensors is found in "A Pd-PdO Film Potentiometric pH Sensor", by Karagounis et al., IEEE Transactions on Biomedical Engineering, Vol. BME-33, No. 2, February 1986 which is hereby incorporated by reference in its entirety.

The chemical sensor 608 is a b 3-electrode configuration that includes a reference electrode 618 comprising any suitable material (e.g., Ag, AgCl), a working electrode 620 (e.g. comprising Ag) and a counter electrode 622 (e.g., comprising Ag). The chemical sensor 608 is of a design typically used in conjunction with voltammetric techniques. It is to be appreciated that other suitable sensor designs, including a 2-electrode or 4-electrode electro-chemical sensor, may be employed. When either an AC or DC voltammetric signal is applied to the working electrode 620, a response current is generated between the working electrode 620 and the counter electrode 622. The applied voltammetric signal can be a symmetric triangular signal, a sinusoidal signal, or any other suitable waveform. The amplitude and frequency of the signal can vary based on the fluid composition and analysis desired. The response current signal parameters vary depending upon the electrochemical processes occurring at the surface of the working electrode 620. The electrochemical processes are a function of the constituent concentrations, and the response current is therefore responsive to these concentrations. The electrochemical sensor is useful for determining the presence of contaminants like water or oxidation product, for example, in a fluid being analyzed. In accordance with one particular aspect of the present invention, the chemical sensor 608 utilizes voltammetric techniques to determine presence of particular chemical additives that relate to lubricity of fluid. For instance, the chemical sensor 608 can be employed to determine presence of ZDDP and/or TCP. Moreover, the chemical sensor 608 can be utilized to alter an electrostatic field to indicate presence of fluids providing enhanced lubricity due to electrostatic field attraction. Alternatively, other sensing elements and/or an independent voltage/current source can be employed in connection with altering an electrostatic field proximate to the sensor elements.

The conductivity sensor 610 is of a two-electrode design, however, it is to be appreciated that other configurations (e.g., four electrode) may be employed. In the preferred embodiment, the two electrodes (624, 626) comprise gold, however, any suitable metal or material may be employed. Two and four electrode conductivity sensors are well known and thus further discussion related thereto is omitted for sake of brevity. Knowledge of the conductivity is also useful for determining if metal wear and/or water is contaminating a fluid, for example.

The temperature sensor 612 provides for determining the temperature of the fluid being analyzed, and is preferably formed from platinum, however, it is to be appreciated that any material (e.g., gold) suitable for carrying out the present invention may be employed. The temperature sensor 612 is patterned on the base 602 in accordance with a predetermined length, width and surface area. Therefore, by knowing the surface area of the temperature detector 612 and the material of which it is made, a temperature of a fluid to which the temperature sensor 612 is exposed may be determined based on the electrical conductivity of the temperature detector 612. Knowledge of fluid temperature is useful in interpreting the health state of the fluid being analyzed because certain fluid parameters (e.g. viscosity) are a function of fluid temperature. Furthermore, the rate of fluid breakdown or additive depletion is also a function of temperature. Therefore, temperature can be utilized in connection with determining lubricity of a fluid within machinery. It is possible using the temperature sensor element 612 or a separate element of a similar to design to heat the fluid in the vicinity of the electrodes. The temperature sensor metalization can function as a resistance heater. The ability to sense the temperature in the vicinity of the heater provides the capability for closed-loop temperature control. The ability to operate the various sensor elements under specific, controlled temperatures is extremely useful in obtaining more accurate and robust data readings and in analyzing the sensor reading results.

Each fluid parameter sensor (e.g. pH/TAN sensor 606, electrochemical sensor 608, conductivity sensor 610, temperature sensor 612) has respective sets of contact pads 628-644 that provide for easy coupling to the respective sensors. The fluid sensor 600 is small having a square area of approximately 4 mm. Accordingly, the fluid sensor 600 is desirable for use in applications where space, weight, and power are at a premium but where accuracy, reliability, and sensitivity of measured data are also at a premium. Furthermore, because the fluid sensor 600 is fabricated in accordance with integrated circuit-like fabrication techniques, large batches of the fluid sensors 600 may be easily and efficiently produced with good production yields, using conventional wafer fabrication facilities. For example, hundreds of sensors can be fabricated on a standard 4-inch wafer using conventional fabrication methods and facilities.

Furthermore, it is to be understood that some sensing devices 604 may be omitted from the fluid sensor 600 and/or different types of sensing devices (e.g., pressure sensor, IR sensor, light sensor, density sensor, light transmission sensor, accelerometer, shear sensor) may be incorporated into the fluid sensor 600. One, some or all of the sensing devices 604 may be replicated "n" number of times (wherein "n" is an integer) on a single fluid sensor 600. Such an embodiment may provide for increased reliability because if one particular sensing device failed there would be like sensing devices serving as backups. Multiple sensing devices of the same type on a single fluid sensor 600 may also afford for increased accuracy as a result of improved signal to noise ratio. The multiple versions of the same sensing element type may span a wide range of sizes, ratios, etc., each of which has a range of optimal sensing accuracy. Together these sensor elements 604 provide for substantial accuracy over a wide range of parameter values. The replicated sensing devices 604 may also improve dynamic range of the fluid sensor 600 as well as versatility (e.g., the fluid sensor 600 may be employed on a wide range of materials and/or fluids). Such an embodiment may also have enhanced integrity because it may be able to sense if a particular sensing device 604 has failed or to identify the type of contaminant (e.g., engine coolant, transmission fluid).

Figure 7:
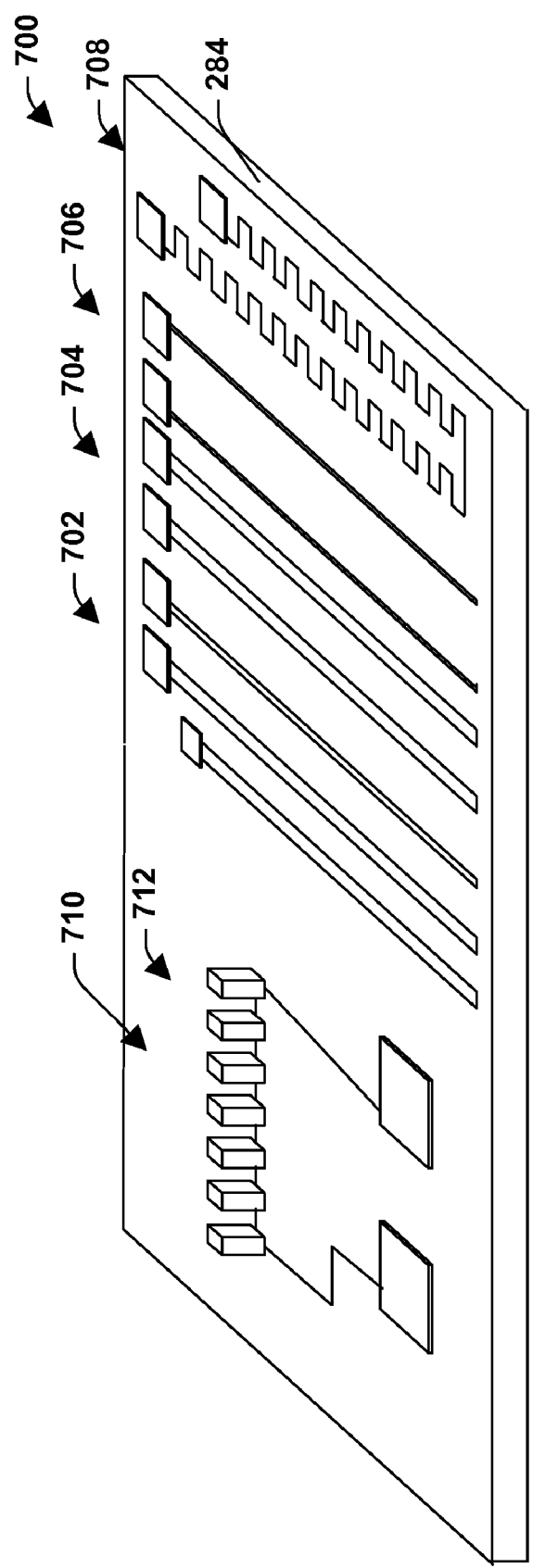
FIG. 7 is an exemplary multi-element sensor that can be utilized in connection with the present invention.

FIG. 7 illustrates another exemplary multi-element sensor 700 that can be utilized in connection with obtaining a measurement of lubricity and/or an FTIR spectrum plot relating to a fluid. The multi-element sensor 700 includes a pH/TAN sensor 702, an electrochemical sensor 704, a conductivity sensor 706, a temperature sensor 708, and a viscosity sensor 710. The pH sensor 702, the electrochemical sensor 704, the conductivity sensor 706, and the temperature sensor 708 are essentially the same as that described in connection with FIG. 6 and therefore further discussion related thereto is omitted for sake of brevity. The viscosity sensor 710 provides for sensing the viscosity of a fluid being analyzed. In short, the viscosity sensor 710 works in conjunction with the temperature sensor 708 to facilitate analyzing viscosity of the fluid being analyzed.

The viscosity sensor 710 includes a plurality (e.g., array) of finger-like elements (e.g., cilia) 712 which are plated with an electrically conductive material. The finger-like elements 712 extend perpendicularly from a surface 714 of the sensor, and the sensor 710 functions based on a phenomena that a dissipative or damping force that resists the motion of the energized finger-like elements 712 results in an increased power demand to maintain oscillation of the finger-like elements 712 at a particular frequency. A fluid of high viscosity will exert a greater damping force on the oscillating finger-like elements 712 than a fluid of lower viscosity. As a result, more power is required to maintain oscillation of the finger-like elements 712 at a particular frequency in a high viscosity fluid than a fluid of lower viscosity. Thus, the viscosity of a fluid may be determined via the micro viscosity sensor 710 of the present invention by monitoring the power required to oscillate the finger-like elements 712 at a particular frequency and/or range of frequencies. Since the viscosity of a fluid is typically a function of fluid temperature (e.g., typically, the higher the fluid temperature the lower the fluid viscosity), the present invention also employs the temperature detector 708 to correlate the temperature of the lubricant or fluid with the aforementioned power requirements to accurately interpret lubricant or fluid viscosity. A more detailed discussion relating to the operation and fabrication of such a viscosity sensor is found in U.S. Pat. No. 6,023,961, entitled MICRO-VISCOSITY SENSOR AND LUBRICATION ANALYSIS SYSTEM EMPLOYING THE SAME, which as mentioned above is hereby incorporated by reference in its entirety.

Figure 8:
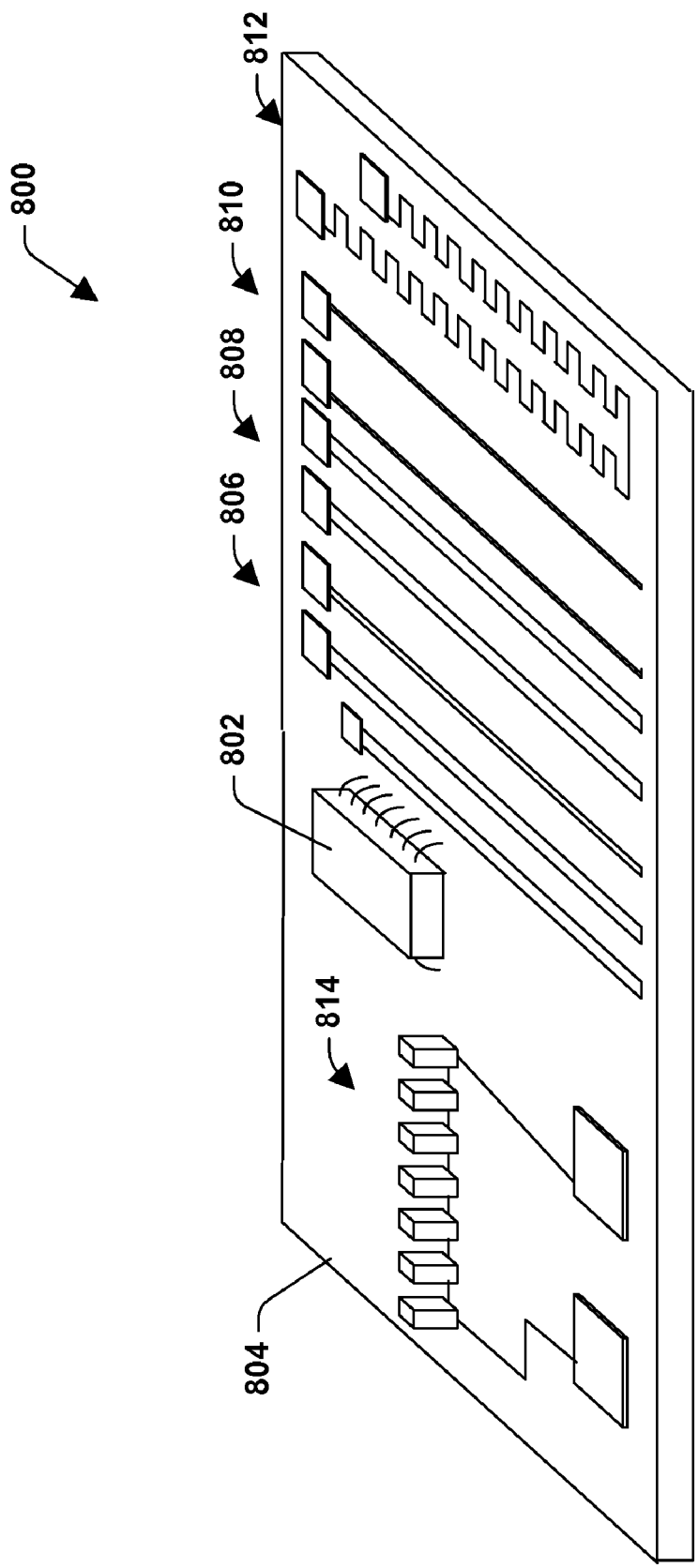
FIG. 8 is an exemplary multi-element sensor that can be utilized in connection with the present invention.

FIG. 8 illustrates another exemplary multi-element sensor 800 that can be employed in connection with the present invention. The multi-element sensor 800 also includes a processor 802 integrated on a semiconductor surface 804. The processor 802 can receive measurements obtained by a plurality of sensing elements, such as a pH/TAN sensor 806, an electrochemical sensor 808, a conductivity sensor 810, a temperature sensor 812, and a viscosity sensor 814. The processor 802 is employed to carry out general operations of the multi-element sensor 800 including data fusion in accordance with an exemplary data fusion framework described in U.S. Pat. No. 6,286,363 entitled INTEGRATED MULTI-ELEMENT LUBRICATION SENSOR AND HEALTH LUBRICANT ASSESSMENT SYSTEM. The processor 802 can be any of a plurality of suitable processors, such as for example: CPU die or processor/logic/storage bonded (flip chip) to the sensor substrate—the sensor elements may be wire bonded to processor I/O connection points. The manner in which the processor 802 can be programmed to carry out the functions relating to the present invention will be readily apparent to those having ordinary skill in the art based on the description provided herein and thus further discussion related thereto is omitted for sake of brevity. Thus, the multi-element sensor 800 provides for a substantially autonomous fluid measurement, analysis, and automatic maintenance system. The multi-element sensor 800 can provide for performing fluid analysis functions as well as affording for self-diagnosis. The multi-element sensor 800 may also be able to verify that it is in a feasible operating regime.

Figure 9:
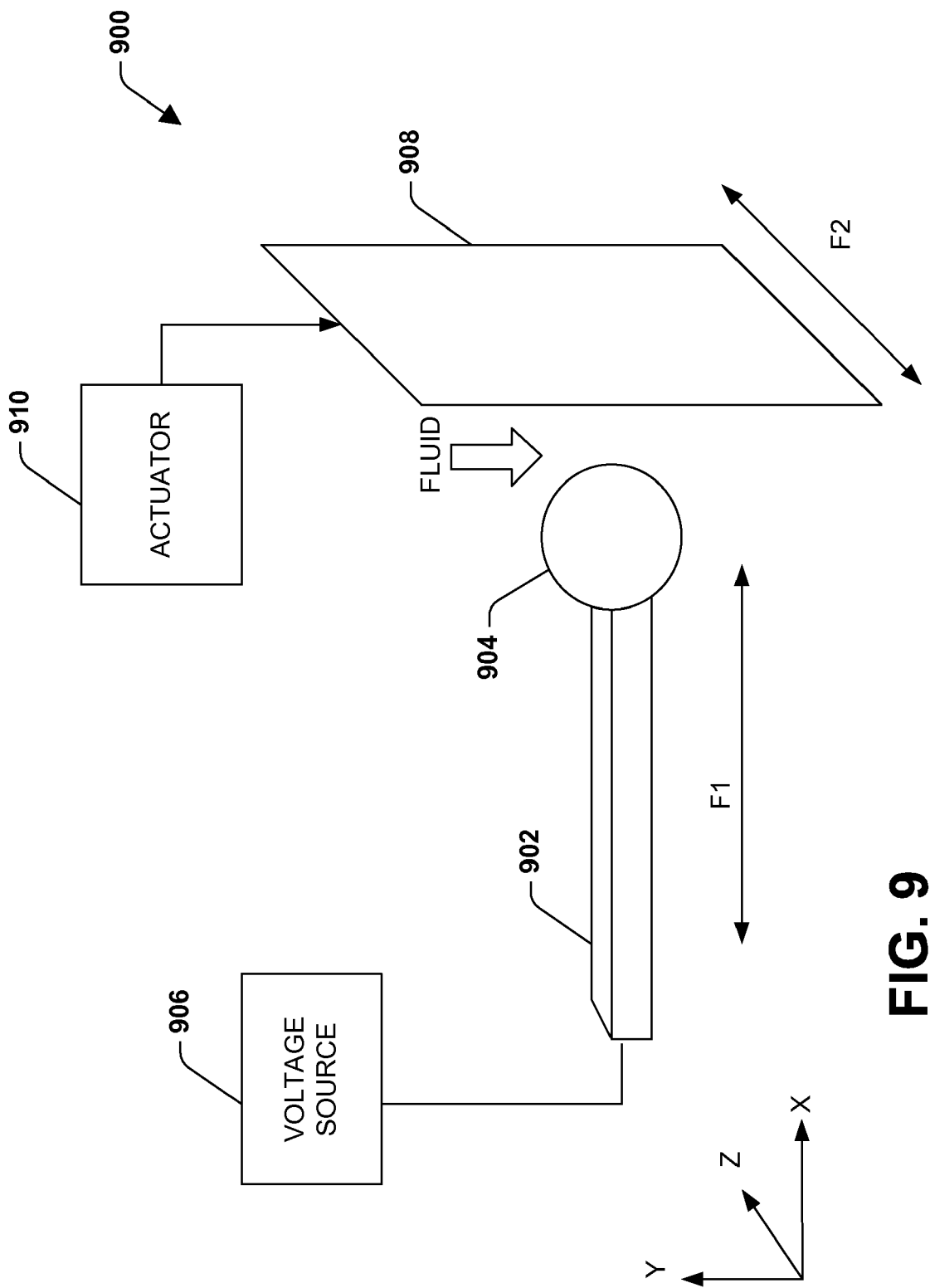
FIG. 9 is an exemplary sensing element that can be utilized to obtain data relevant to lubricity of a fluid in accordance with one aspect of the present invention.

Turning now to FIG. 9, an exemplary sensing element 900 for obtaining a measurement relating to lubricity of a fluid is illustrated. The sensing element comprises a piezoelectric actuator beam 902 with a contact surface 904 attached to an end of the beam. While the contact surface 904 is illustrated as a sphere, it is to be understood that shape of the contact surface 904 is arbitrary, and any suitably shaped contact surface can be employed. In particular, different tip geometries (e.g. round tip, planar tip, grooved tip) will result in different measurement values and indicate different fluid properties. A voltage source 906 can actuate the beam 902, producing a force F1 towards a wear surface 908. The wear surface 908 is associated with an actuator 910 to move the wear surface 908 perpendicularly to the beam 902 (e.g., a force F2 is generated perpendicular to force F1). While forces F1 and F2 are illustrated as being perpendicular to one another, the direction of forces is arbitrary. All that is required is that the contact surface 904 is contacting the wear surface 908 and the contact surface 904 and wear surface 908 are moving laterally relative to one another to provide friction. The sensing element 900 resides within the fluid, thus enabling fluid to lubricate between the contact surface 904 and the wear surface 908. A measurement relating to lubricity is obtained via monitoring forces required to move the contact surface 904 over a particular distance along the wear surface 908 for a given surface contact pressure established by force F1. For example, an application of forces F1 and F2 in a positive direction will result in movement of a particular distance of the contact surface 904 relative to the wear surface 908. Such measurements can be relayed to a data filtering/fusion network (along with various other measurements relating to lubricity of a fluid) to obtain a robust measurement of lubricity of the fluid.

Figure 10:
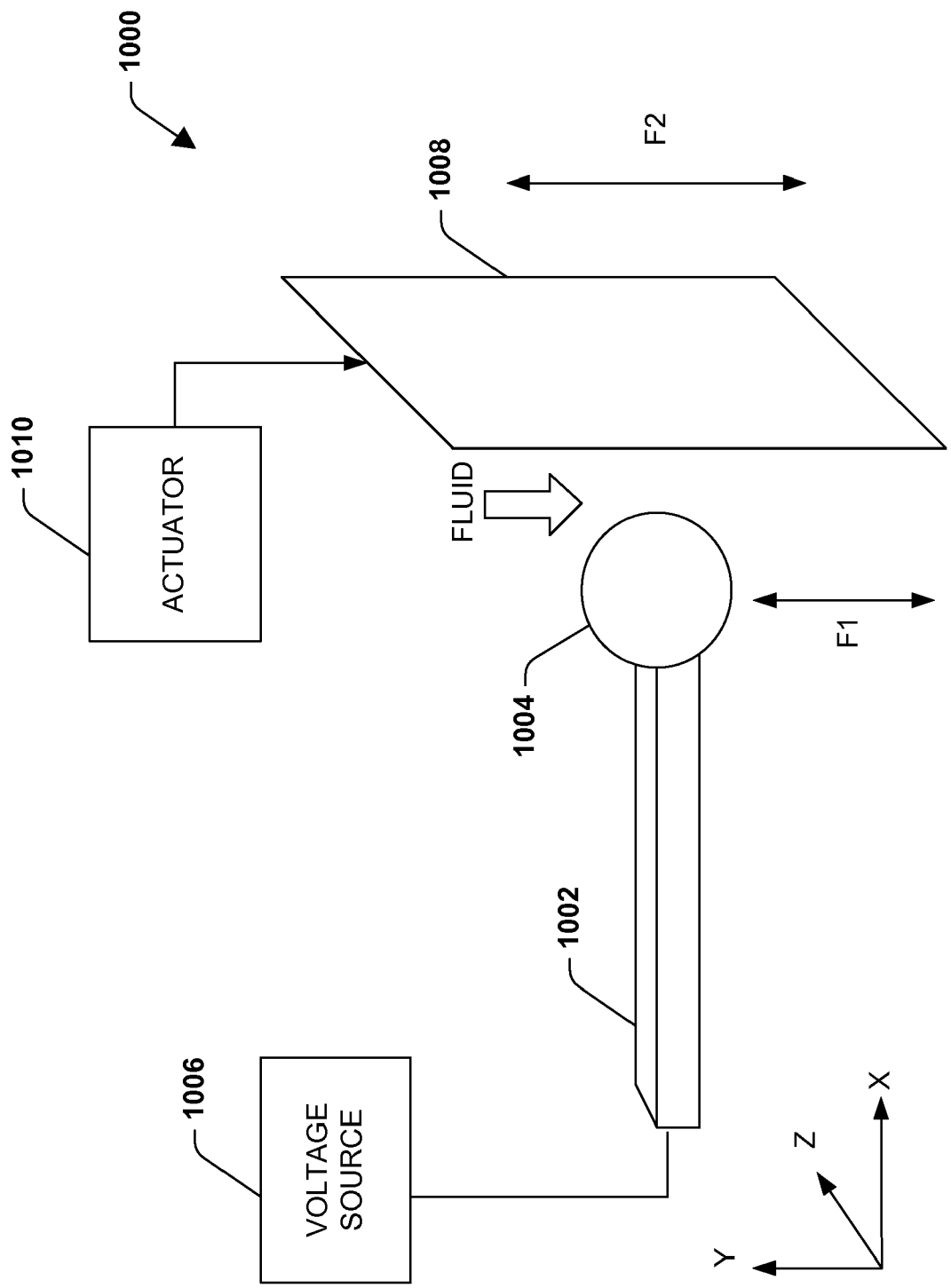
FIG. 10 is an exemplary sensing element that can be utilized to obtain data relevant to lubricity of a fluid in accordance with one aspect of the present invention.

Now referring to FIG. 10, an exemplary sensor element 1000 that can be employed in connection with the present invention is illustrated. The sensing element 1000 includes a piezoelectric actuator beam 1002 that is connected to a contact surface 1004. The contact surface 1004 can be movable in a y-direction with a force F1 via connecting the actuator beam 1004 to a voltage source 1006. A wear surface 1008 driven can also be movable in the y-direction via a force F2 provided by an actuator 1110. The contact surface 1004 can be moved at different distances from the wear surface 908. The contact surface 1004 can further be moved in the vertically-direction in close proximity to the wear surface 1008. The actuator 1010 for the wear surface 1008 exerts the force F2 on the wear surface 1008. As the contact surface 1004 moves vertically (e.g., in either positively or negatively in the y-direction) near the wear surface 1008 it will exert a moving force through lubricating film to cause the wear surface 1008 to also move vertically. A sensor and controller (not shown) connected to the actuator 1010 can be readily developed to prevent the wear surface 1008 from moving. An amount of force required to keep the wear surface 1008 stationary is substantially similar to a fluid-transmitted force between the two surfaces 1004 and 1008. The control energy required provides an indication of the lubricity of the fluid. Such measurements can be relayed to a data filtering/fusion network (along with various other measurements relating to lubricity of a fluid) to obtain a robust measurement of lubricity of the fluid.

Figure 11:
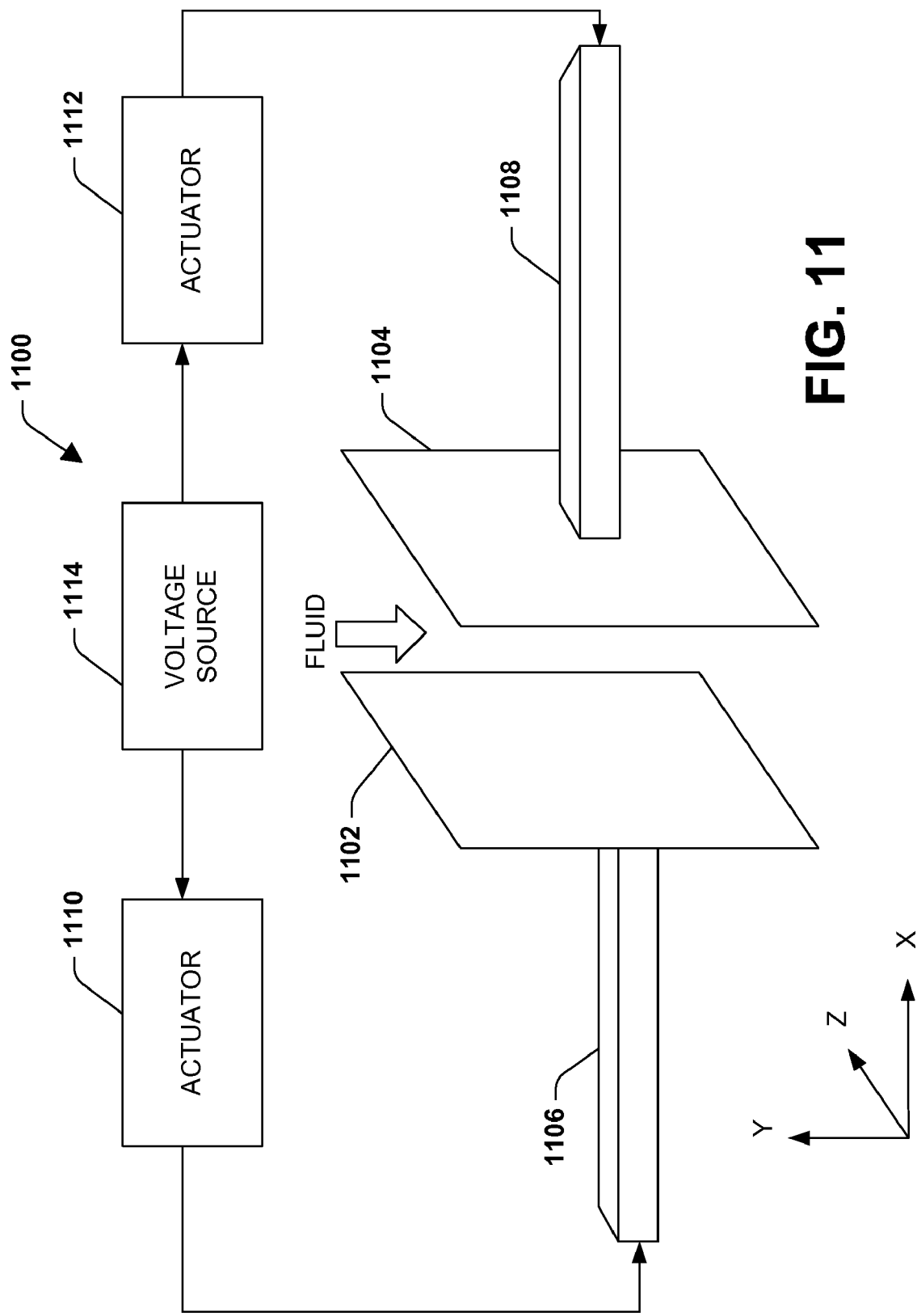
FIG. 11 is an exemplary sensing element that can be utilized to obtain data relevant to lubricity of a fluid in accordance with one aspect of the present invention.

Turning now to FIG. 11, another exemplary sensing element 1100 that facilitates attainment of data relevant to lubricity of a fluid is illustrated. The sensing element 1100 operates in a substantially similar manner as the sensing element 900 illustrated in FIG. 9. The sensing element includes two surfaces 1102 and 1104 that are positioned at the end of beams 1106 and 1108, respectively. Actuators 1110 and 1112 can be provided to press the two surfaces 1102 and 1104 together via driving the beams 1106 and 1108 towards one another. A voltage source 1114 provides controlled power to the actuators 1110 and 1112, respectively. In an alternative embodiment, actuators 1110 and 1112 are not necessary as the beams 1106 and 1108 are themselves piezoelectric actuators that can be deformed upon application of a voltage from the voltage source 1114. The surfaces 1102 and 1104 are thereafter moved with respect to one another to obtain an indication of lubricity of fluid that resides between the surfaces 1102 and 1104. For instance, the actuator 1110 can provide a force to the beam 1106 in a positive x-direction and a positive y-direction, while the actuator 1112 provides a force in the negative x-direction to ensure the surfaces are in contact. As the surfaces 1102 and 1104 are frictionally moved relative to one another, the force required for such movement indicates lubricity of the fluid. The force-distance data can be relayed to a sensor filtering/fusion component (not shown) to facilitate determination of lubricity within the fluid. Alternatively the surfaces 1102 and 1104 can be indexed to be proximate to one another and then moved laterally in opposite directions. The force required for movement indicates lubricity of the fluid. In accordance with another aspect of the present invention, the surfaces 1102 and 1104 can be indexed to be proximate to one another and thereafter moved away from each other. A force required to separate the surfaces 1102 and 1104 can indicate a measure of "stickiness" of the fluid (e.g., "stickiness is indicative of lubricity).

Figure 12:
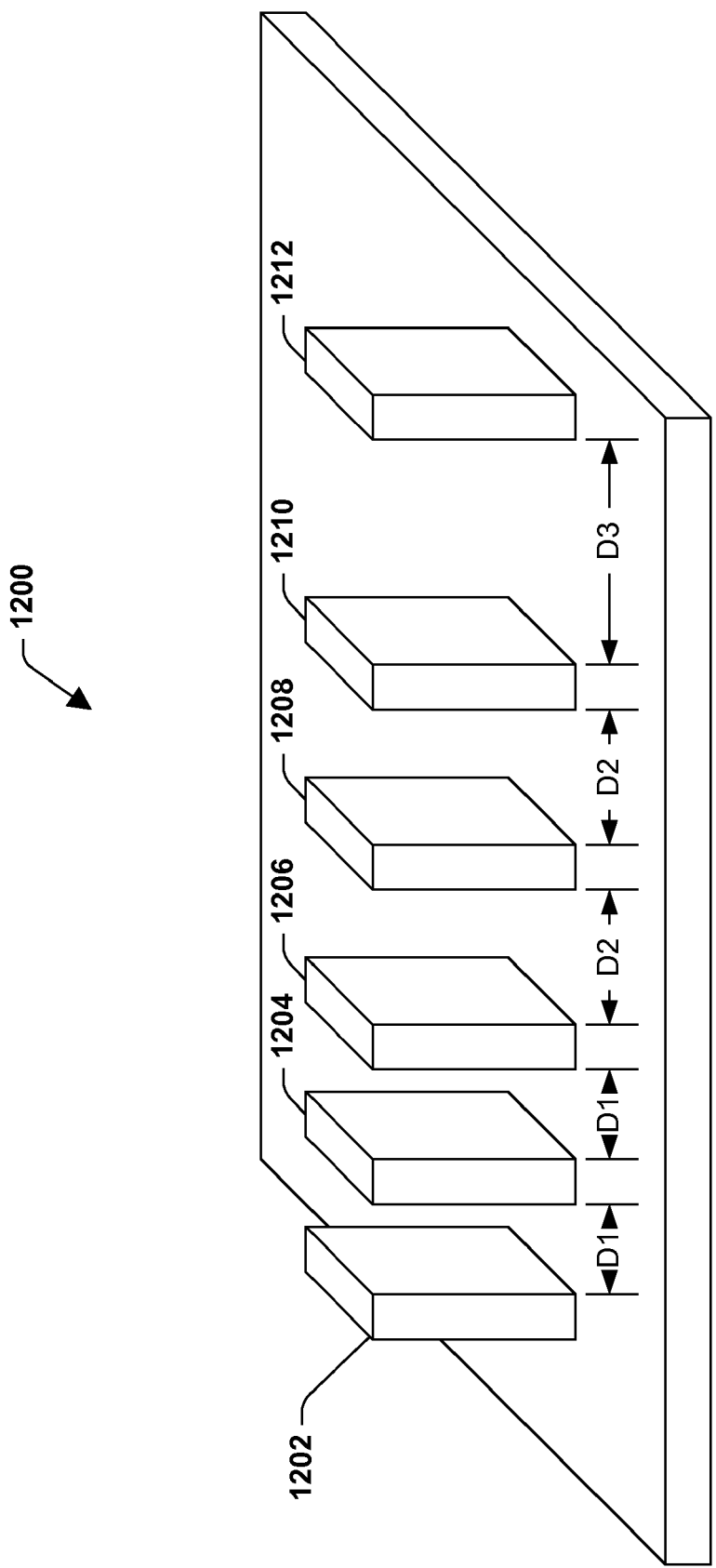
FIG. 12 is an exemplary sensing element that can be utilized to obtain data relevant to lubricity of a fluid in accordance with one aspect of the present invention.

Now referring to FIG. 12, an exemplary sensing element 1200 that facilitates attainment of a parameter relating to lubricity of a fluid in machinery is illustrated. The sensing element 1200 includes a plurality of finger-like elements 1202-1212 conventionally utilized to measure viscosity, wherein several of the finger-like elements 1202-1212 are disparately spaced. As described infra, a measurement of viscosity can be obtained via providing a sufficient amount of power to vibrate the finger-like elements 1202-1214, and thereafter relaying required power and particular frequency to a data fusion network. The finger-like elements, however, can further be employed to obtain data relating to lubricity via decreasing power to the finger-like elements 1202-1214 and determining an ability of the lubrication to adhere to the surface of the finger-like elements 1202-1214. For instance, an ability of fluid to adhere to surfaces of finger-like elements 1202 and 1204, which are separated by a distance of D1, can be compared to an ability of the fluid to adhere to surfaces of elements 1210 and 1212, which are separated by a greater distance D3. Such measurements are related to lubricity of the fluid. Furthermore, multiple viscosity sensors (each comprising a plurality of finger-like elements) can be utilized, wherein each viscosity sensor has disparate spacing between finger-like elements. Such an embodiment can be beneficial in that fabrication of the viscosity sensors can be more efficient, as disparate spacing of finger-like elements is not required for a single viscosity sensor.

In accordance with another aspect of the present invention, the finger-like elements 1202-1214 can each be coated with a disparate surface finish. Power can be provided to vibrate the finger-like elements 1202 at a particular frequency, and thereafter the power can be slowly removed. An ability of fluid to adhere to particular surface finishes of the finger-like elements 1202-1212 is indicative of lubricity of the fluid. Measurements relating to an ability to adhere to surfaces of the finger-like elements can be relayed to a data filtering/fusion network in connection with providing a measurement of lubricity of the fluid. Information obtained from a separate MEMs viscosity sensing element (not shown) can further increase accuracy of the derived lubricity value. It is also possible to vibrate the finger-like elements 1202-1212 at a varying sinusoidal frequency. Sweeping a wide frequency range and monitoring displacement of the finger-like elements 1202-1204 can provide a more accurate measure of lubricity.

Figure 13:
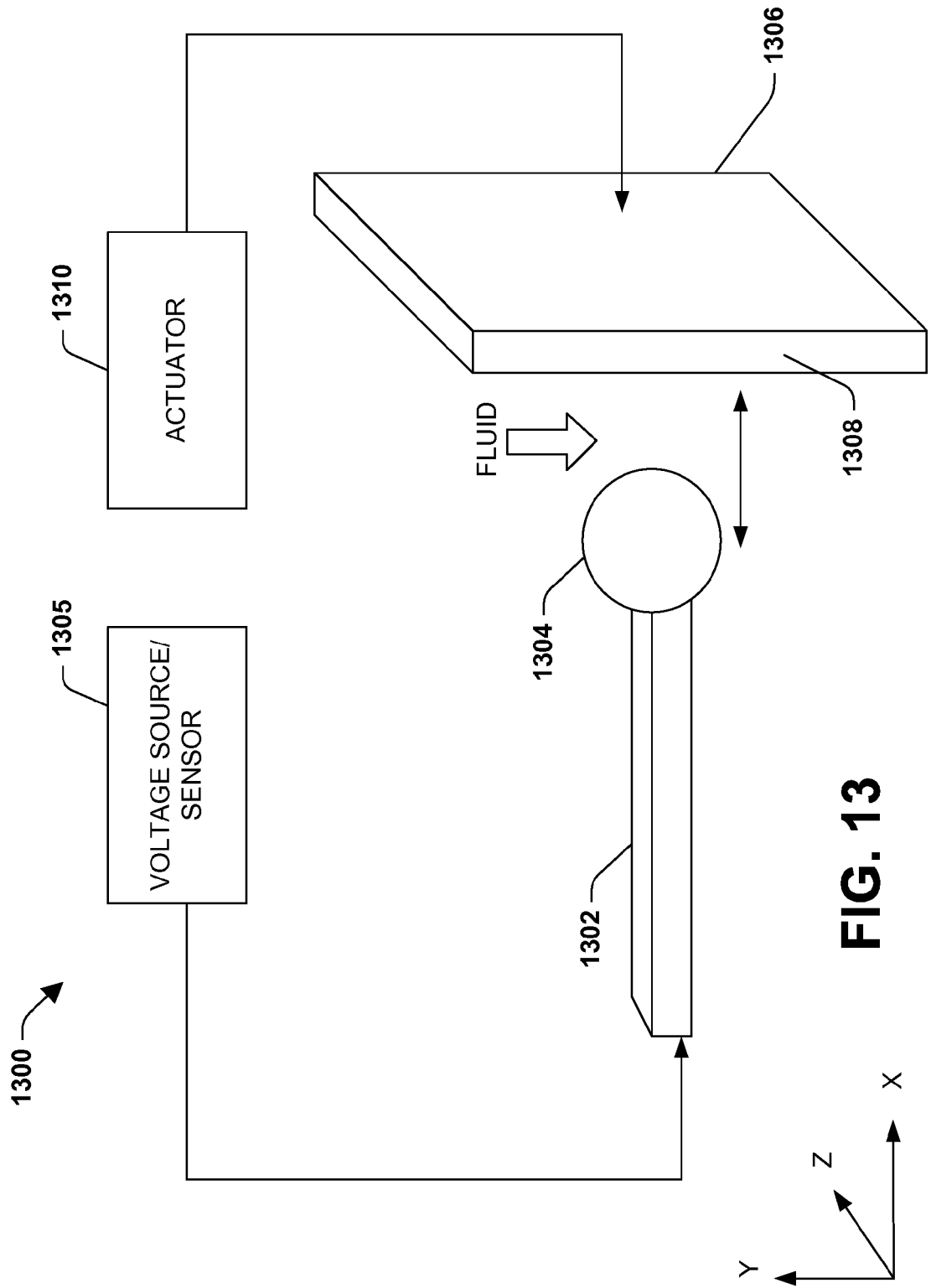
FIG. 13 is an exemplary sensing element that can be utilized to obtain data relevant to lubricity of a fluid in accordance with one aspect of the present invention.

Now turning to FIG. 13, an exemplary sensing element 1300 employed to obtain data relevant to lubricity of a fluid is illustrated. The element 1300 includes a piezoelectric beam 1302 connected to a contact surface 1304. The piezoelectric beam 1302 is operatively coupled to a voltage source/sensor 1305 that delivers voltages to the piezoelectric beam 1302, thereby distorting the beam 1302 and forcing the contact surface 1304 to contact a wear surface 1306. Moreover, application of a voltage to the beam 1302 can cause a force resulting friction between the contact surface 1304 and the wear surface 1306 (e.g., the contact surface 1304 and the wear surface 1308 move relative to one another in the y-z plane). The wear surface 1306 is coated with an insulating layer 1308, and is operably coupled to an actuator 1310 that facilitates generating friction between the contact surface 1304 and the wear surface 1306. As the wear surface 1306 and the contact surface 1304 move across one another, the insulating layer 1308 will wear. Existence of a conductive path, as well as amount of conductivity, is relevant to lubricity of fluid between the contact surface 1304 and the wear surface 1306. Such data can thereafter be received by a data filtering/fusion network, which can employ the data in connection with determining an amount of lubricity in the fluid.

In an alternative embodiment, rather than an insulating layer the wear surface 1306 can include a relatively thick material 1308 that wears readily. A displacement measure of the wear surface can be utilized to obtain a measurement relevant to lubricity of lubricant. By maintaining a constant force between the contact surface 1304 and the wear surface 1306 while the surfaces 1304 and 1306 are repeatedly moved in close proximity to each other, a measurement can be obtained of displacement of the wear surface 1306 due to wear. For example, a capacitive value of the material 1308 can be monitored to determine an amount of wear. Such amount of wear can be utilized in connection with obtaining a measurement of lubricity. While the above exemplary embodiments employ piezoelectric material and various actuators, it is to be understood that any method of creating friction between two surfaces is contemplated and intended to fall within the scope of the hereto-appended claims.

Figure 14:
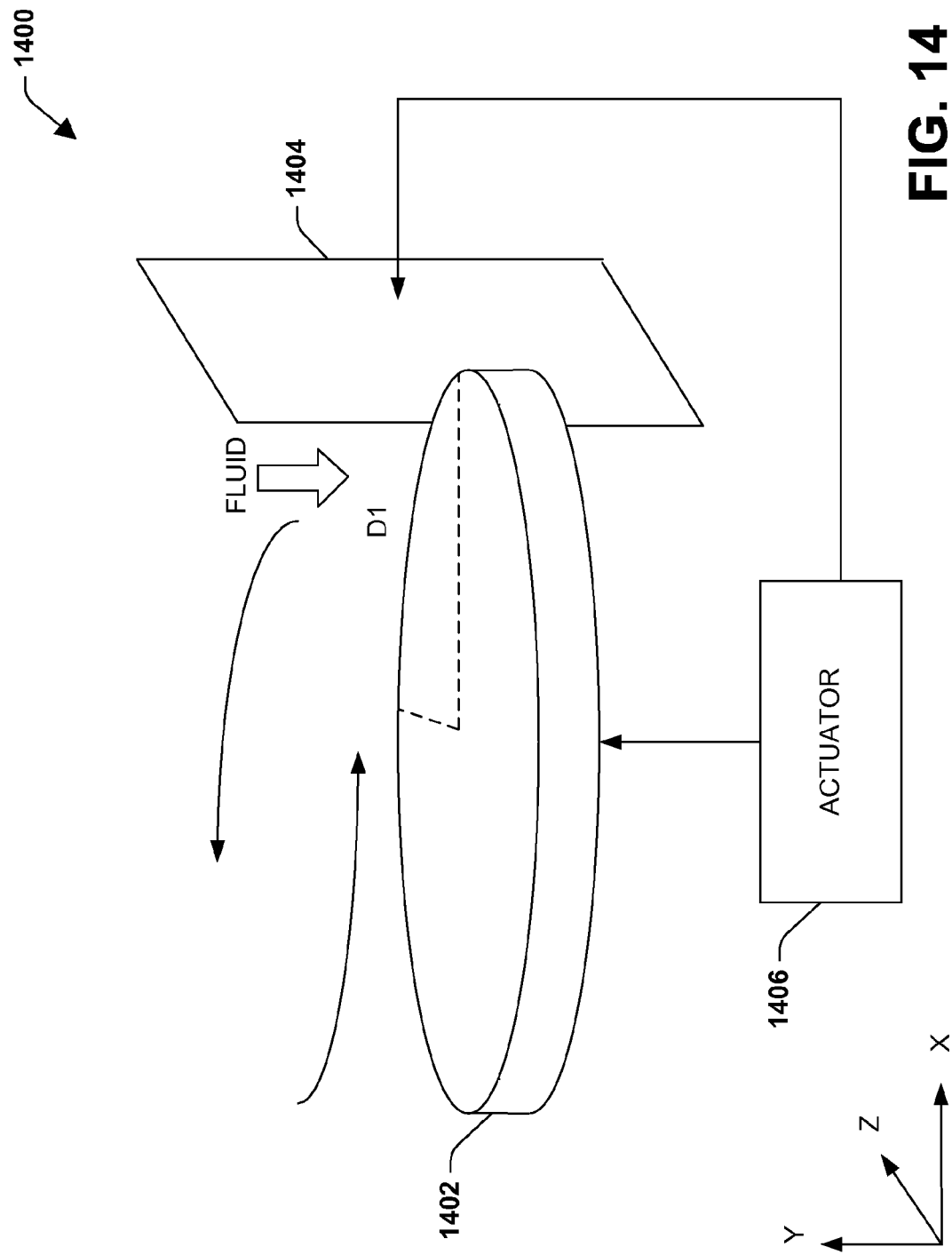
FIG. 14 is an exemplary sensing element that can be utilized to obtain data relevant to lubricity of a fluid in accordance with one aspect of the present invention.

Now regarding FIG. 14, an exemplary sensing element 1400 employed to obtain data relevant to lubricity of a fluid is illustrated. The element 1400 comprises a rotating MEMs disk 1402 that tangentially contacts a wear surface 1404. An actuator 1406 rotates the MEMs disk 1402 and provides a force to the wear surface 1404 requiring the disk 1402 and the wear surface 1404 to contact on another. Forces utilized to rotate the disk 1402 and to force the wear surface 1404 to contact the disk can be monitored together with relative distance traveled between the disk 1402 and the wear surface 1404. Amounts of force required to rotate the disk 1402 a distance D1 given presence of a lubricating fluid is relevant to lubricity of the fluid. Such measurements can be received by a data filtering/fusion network in connection with generating a measurement of lubricity. It is further to be understood that a force required to stop the rotating disk can be indicative of lubricity.

In another operation of this device 1400 (and other similar devices), the surface 1404 can be a wear surface constructed of relatively thick material that readily wears or abrades. The displacement of the wear surface 1404 required to maintain a steady pressure on the rotating disk 1402 is a measure of lubricity. Alternatively, a holding force required to keep the surface 1404 stationary and not move tangentially to the rotating disk 1402 is indicative of lubricity. Such measurements can be received by a data filtering/fusion network in connection with generating a measurement of lubricity.

Figure 15:
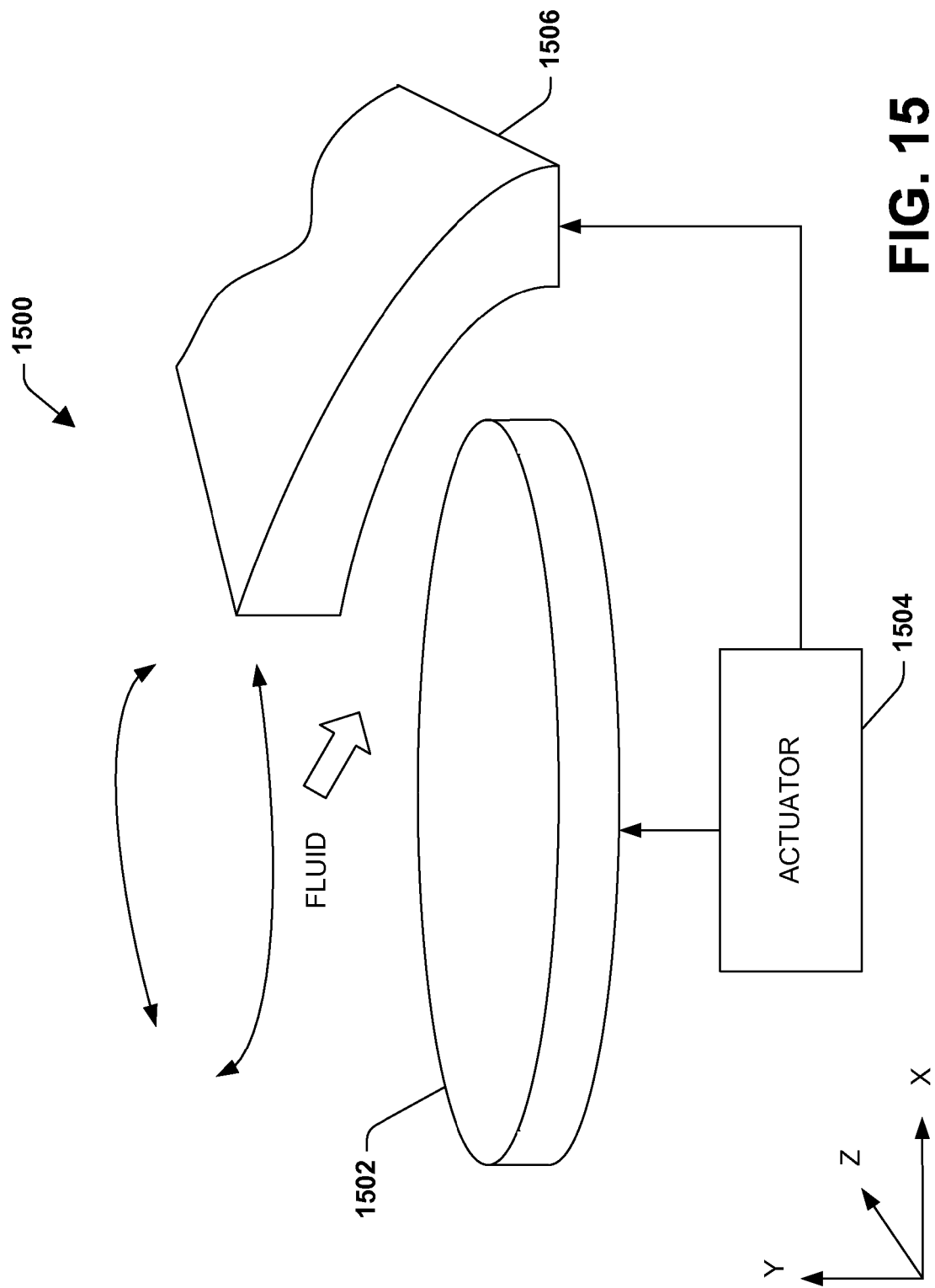
FIG. 15 is an exemplary sensing element that can be utilized to obtain data relevant to lubricity of a fluid in accordance with one aspect of the present invention.

Now referring to FIGS. 15-21, a plurality of exemplary devices that can be employed in connection with measuring lubricity of a fluid are illustrated. Turning first to FIG. 15, a sensing element 1500 that includes a rotary MEMs disk 1502 is displayed. The disk 1502 is operably coupled to an actuator 1504 that effectuates rotating the disk 1502, and can further provide moving the disk 1502 in an x-direction, y-direction, z-direction, or any suitable combination thereof. The disk 1502 can be positioned proximate to a wear surface 1506, wherein the wear surface 1506 is fabricated to provide a substantially match shape with the disk (e.g., the wear surface can be an arc with radius similar to the radius of the disk 1502). The wear surface 1506 is movable in any suitable direction, and can be positioned proximate to the rotating disk via the actuator 1504 or another actuator (not shown). A force required to rotate the disk 1502 a particular distance can be indicative of lubricity of a fluid. Furthermore, a force necessary to stop the disk 1502, a force necessary to inhibit movement of the wear surface 1506, and a force required to separate the disk 1502 and the wear surface 1506 are related to lubricity of a fluid that resides between the disk 1502 and the wear surface 1506. Moreover, as discussed above, the wear surface 1506 can be provided with an insulation layer and/or a readily wearable surface to facilitate determination of lubricity of a fluid.

Figure 16:
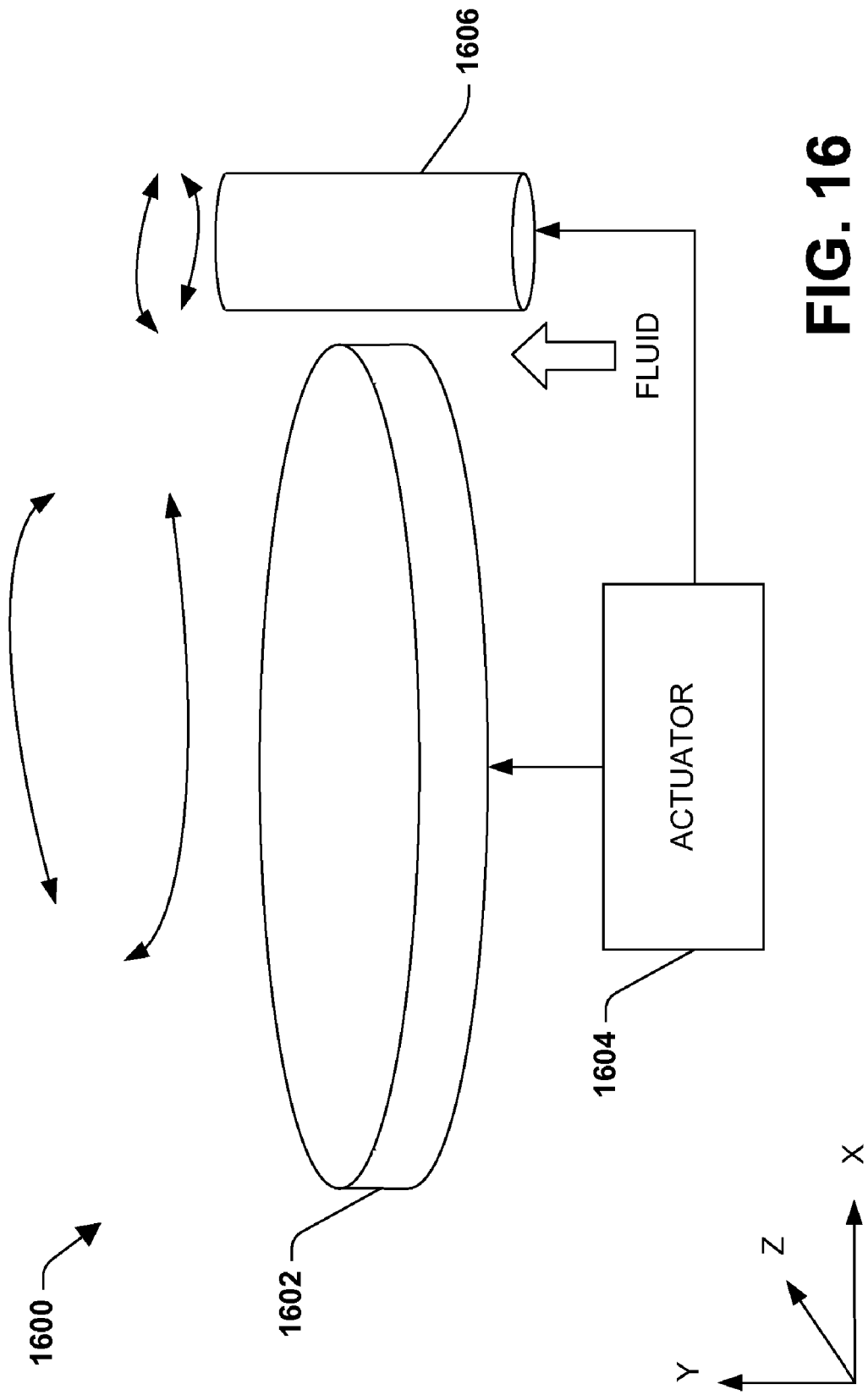
FIG. 16 is an exemplary sensing element that can be utilized to obtain data relevant to lubricity of a fluid in accordance with one aspect of the present invention.

Now referring to FIG. 16, a sensing element 1600 includes a rotary MEMs disk 1602 that is responsive to an actuator 1604. For example, the actuator 1604, can facilitate rotating the disk, as well as moving the disk in any suitable linear direction. The disk 1602 can be positioned proximate to a cylindrical wear surface 1606 with an axis of rotation parallel to the axis rotation of the disk 1602, wherein the wear surface 1606 can also be rotated and moved in any suitable direction via the actuator 1604 (or a disparate actuator). For instance, the wear surface 1606 can be rotated about its axis as well as have a force applied to such wear surface 1606 to move it along the perimeter of the disk 1602. Forces required to move the disk 1602 and/or the wear surface 1606 a particular distance and/or rotate at a particular rate, as well as forces required to stop the disk 1602 and/or the wear surface 1606 can be indicative of lubricity of a fluid.

Figure 17:
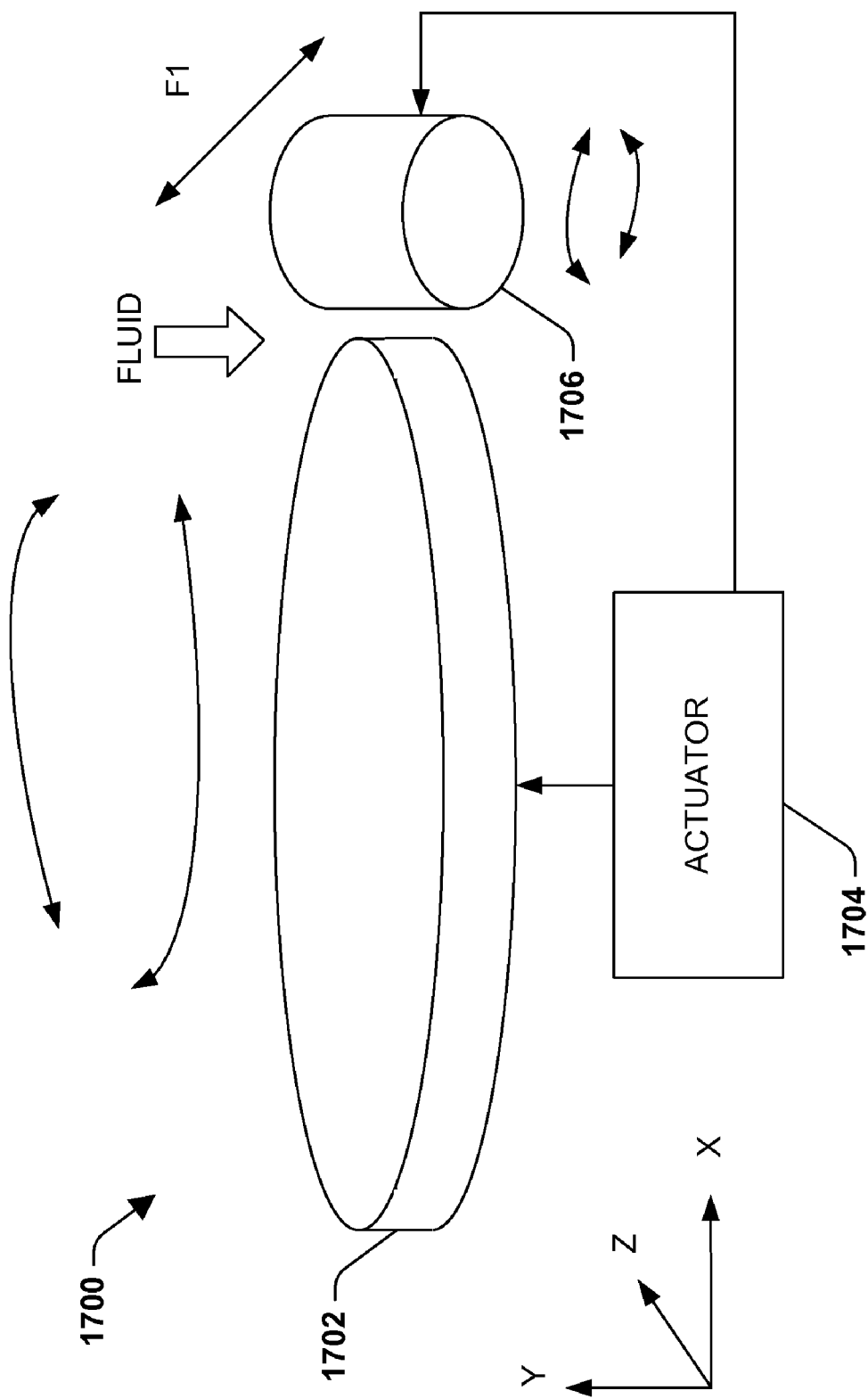
FIG. 17 is an exemplary sensing element that can be utilized to obtain data relevant to lubricity of a fluid in accordance with one aspect of the present invention.

Turning now to FIG. 17, a similar sensing element 1700 to the sensing element 1600 (FIG. 16) is displayed. A rotating MEMs disk 1702 driven by an actuator 1704 is positioned proximate to a cylindrical wear surface 1706 that is likewise driven by the actuator 1704 (or a disparate actuator). For example, the wear surface 1706 can be rotated about its axis and/or have a force F1 applied to facilitate rotation around the axis of the disk 1702. Axes of rotation of the disk 1702 and the wear surface 1706 can be substantially perpendicular to one another. Forces required to rotate the disk 1702 and/or the wear surface 1706 a particular distance, forces required to stop motion of the disk 1702 and/or the wear surface 1706, as well as forces necessary to separate the disk 1702 and the wear surface 1706 can be indicative of lubricity of a fluid.

Figure 18:
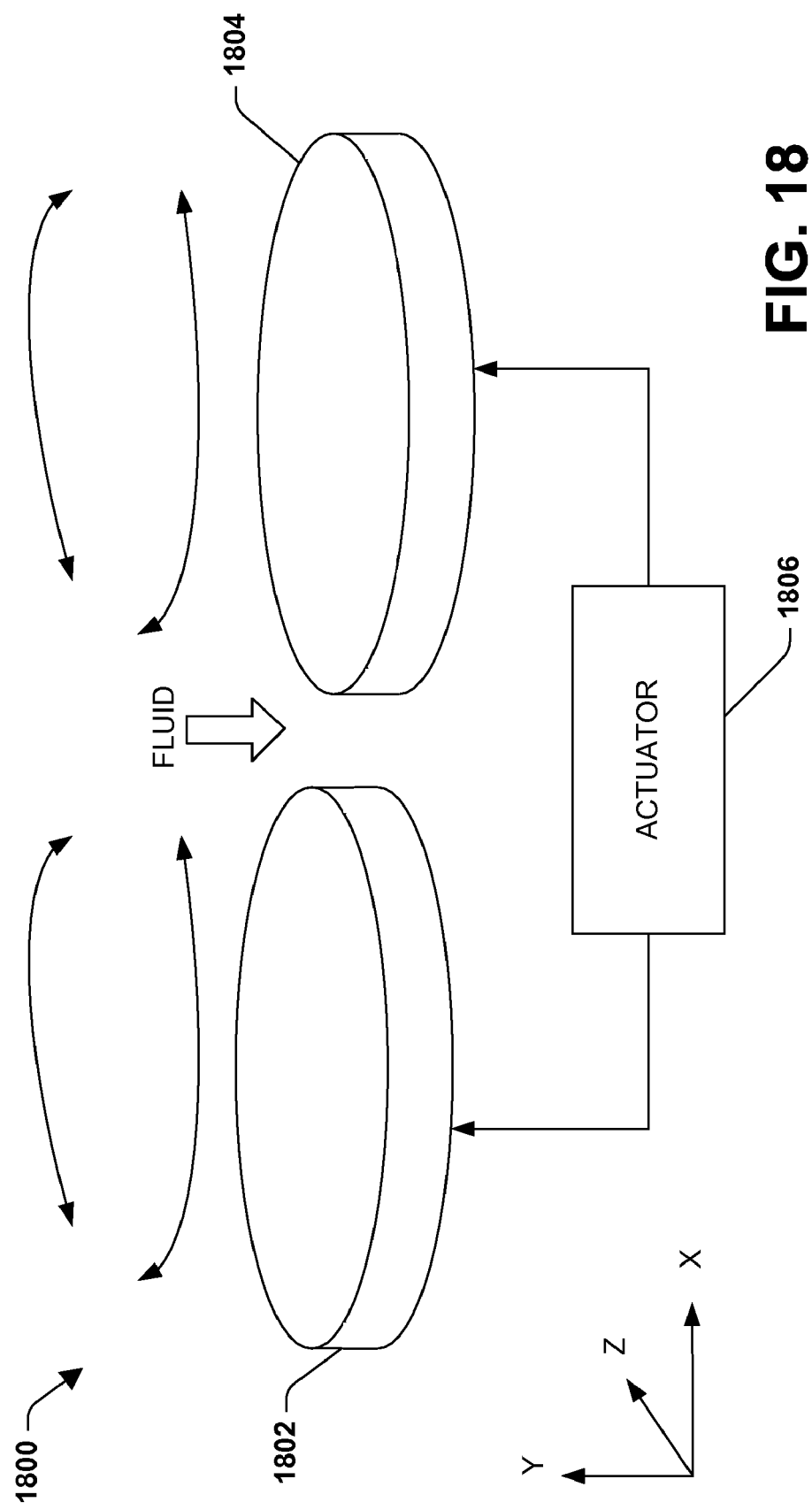
FIG. 18 is an exemplary sensing element that can be utilized to obtain data relevant to lubricity of a fluid in accordance with one aspect of the present invention.

Now regarding FIG. 18, an exemplary sensing element 1800 that can be employed in connection with determining lubricity of a fluid is illustrated. The element 1800 comprises two rotary disks 1802 and 1804 that have axes or rotation substantially parallel to one another. The disks are rotated and/or moved in any suitable direction by an actuator 1806. Alternative, each disk can be rotated and/or moved by disparate actuators (not shown). In this exemplary embodiment, edges of the rotary disks 1802 and 1804 are moved relative to one another. Forces required to rotate a particular disk a particular distance, forces required to inhibit movement of one or more disks, and/or forces necessary to separate the disks 1802 and 1804 can be indicative of lubricity of a fluid.

Figure 19:
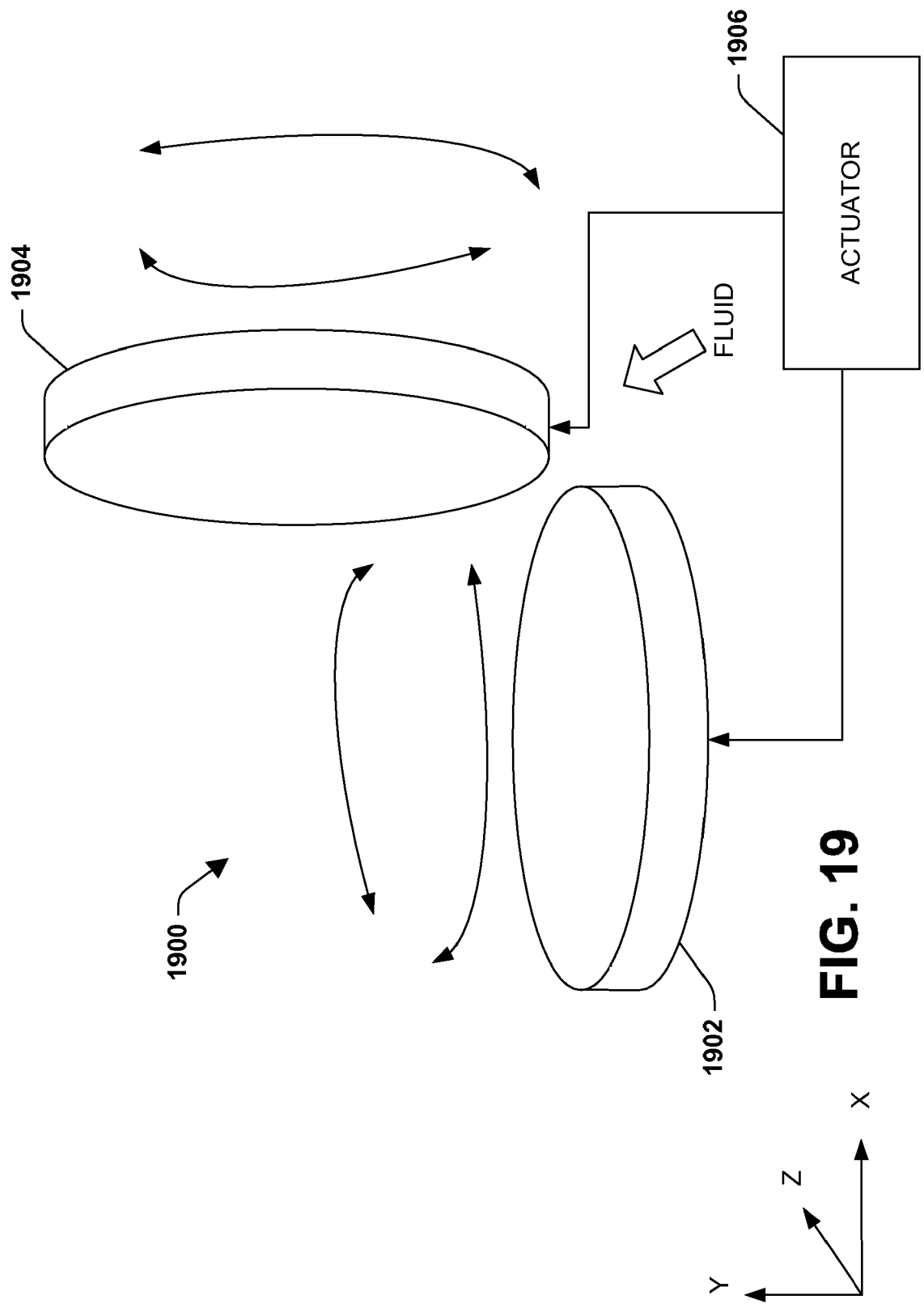
FIG. 19 is an exemplary sensing element that can be utilized to obtain data relevant to lubricity of a fluid in accordance with one aspect of the present invention.

Referring now to FIG. 19, another exemplary sensing element 1900 that can facilitate determining lubricity of a fluid is illustrated. The element 1900 includes two rotary disks 1902 and 1904 that have axes of rotation substantially perpendicular to one another. In disks 1902 and 1904 can be rotated about their axes, rotated about each other's axes, and/or moved in any suitable linear direction. An actuator 1906 (or a plurality of actuators) can be provided to facilitate such movement of the rotating disks 1902 and 1904. In this exemplary embodiment, edges of the rotary disks 1902 and 1904 are aligned with one another. Forces required to rotate a particular disk a particular distance, forces required to inhibit movement of one or more disks, and/or forces necessary to separate the disks 1902 and 1904 can be indicative of lubricity of a fluid.

Figure 20:
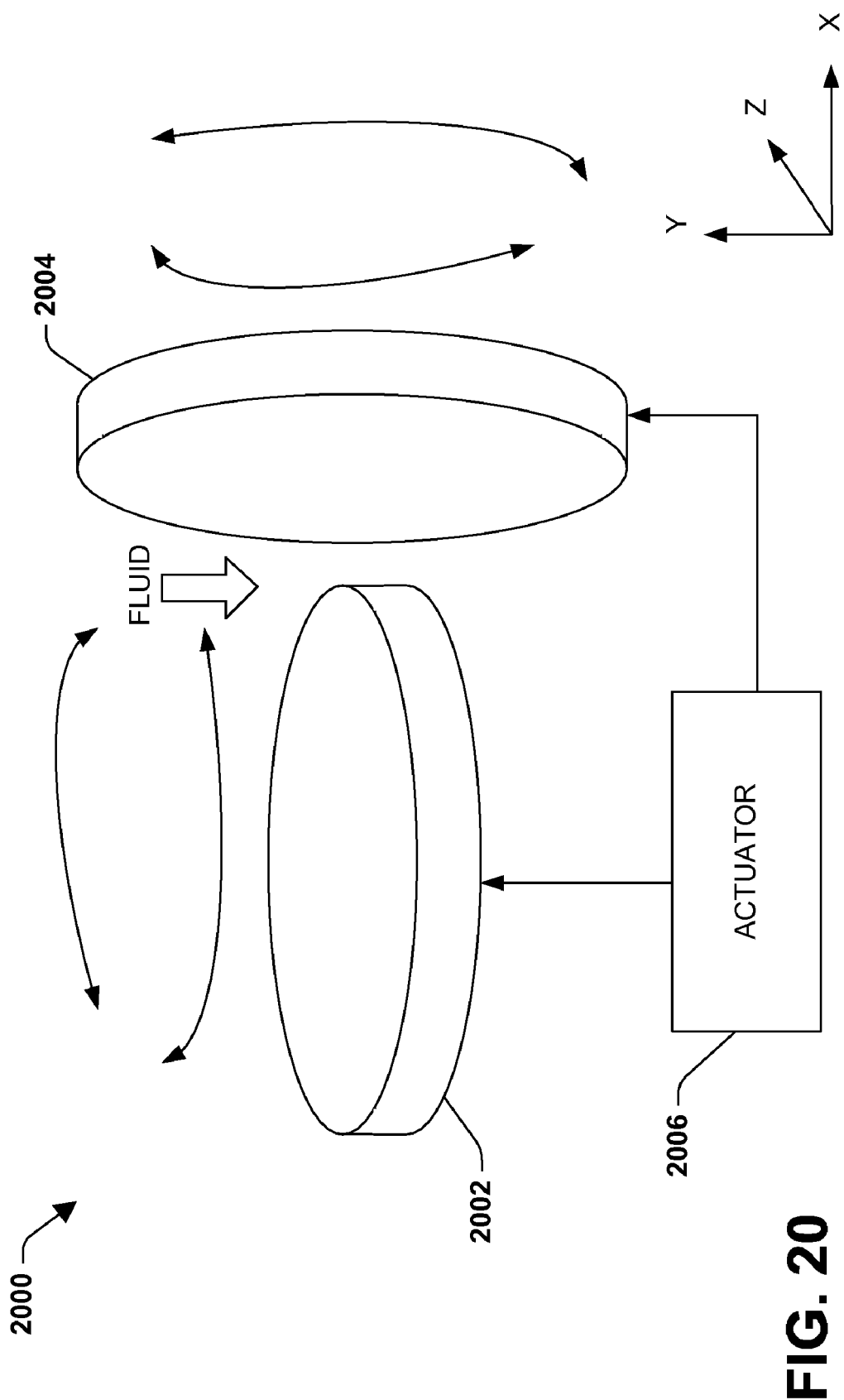
FIG. 20 is an exemplary sensing element that can be utilized to obtain data relevant to lubricity of a fluid in accordance with one aspect of the present invention.

Now turning to FIG. 20, an exemplary sensing element 2000 that facilitates measuring a degree of lubricity of a fluid is displayed. The element 2000 comprises two rotary disks 2002 and 2004 that can be rotated and/or moved in any suitable linear direction via an actuator 2006 or plurality of actuators. For example, the disk 2004 can be rotated about its axis and simultaneously rotated about the axis of the disk 2002. The actuator 2006 can position the two disks proximate to one another, and forces required to rotate a particular disk a particular distance, forces required to inhibit movement of one or more disks, and/or forces necessary to separate the disks 2002 and 2004 can be indicative of lubricity of a fluid.

Figure 21:
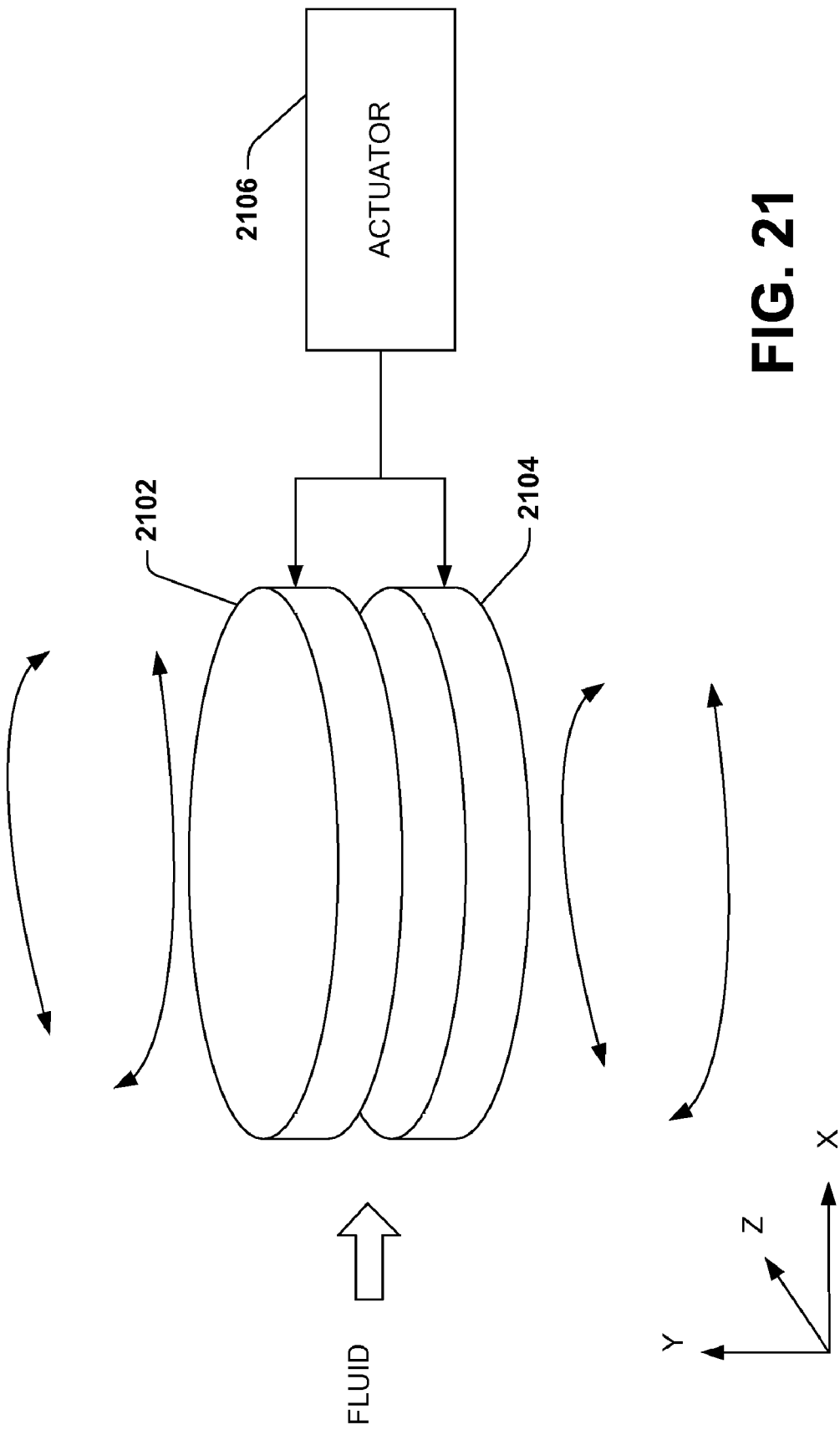
FIG. 21 is an exemplary sensing element that can be utilized to obtain data relevant to lubricity of a fluid in accordance with one aspect of the present invention.

Referring now to FIG. 21, another exemplary sensing element 2100 that can be employed in connection with measuring a degree of lubricity of a fluid is illustrated. The element includes rotary disks 2102 and 2104, wherein faces of the disks 2102 and 2104 are positioned proximate to one another. The disks 2102 and 2104 can be rotated and moved in any suitable linear direction by an actuator 2106 (or a plurality of actuators). Forces required to rotate a particular disk a particular distance, forces required to inhibit movement of one or more disks, and/or forces necessary to separate the disks 2002 and 2004 can be indicative of lubricity of a fluid. Moreover, an amount of wear on the faces of the disks 2102 and 2104 can indicate a degree of lubricity of a fluid. In accordance with another aspect of the present invention, one or more of the faces of the disks 2102 and 2104 can be provided with a insulating material and/or a thick surface of readily wearable material. A conductive path between the faces and/or measure of capacitance with respect to one or more of the faces can be measured to indicate a degree of lubricity of the fluid.

Figure 22:
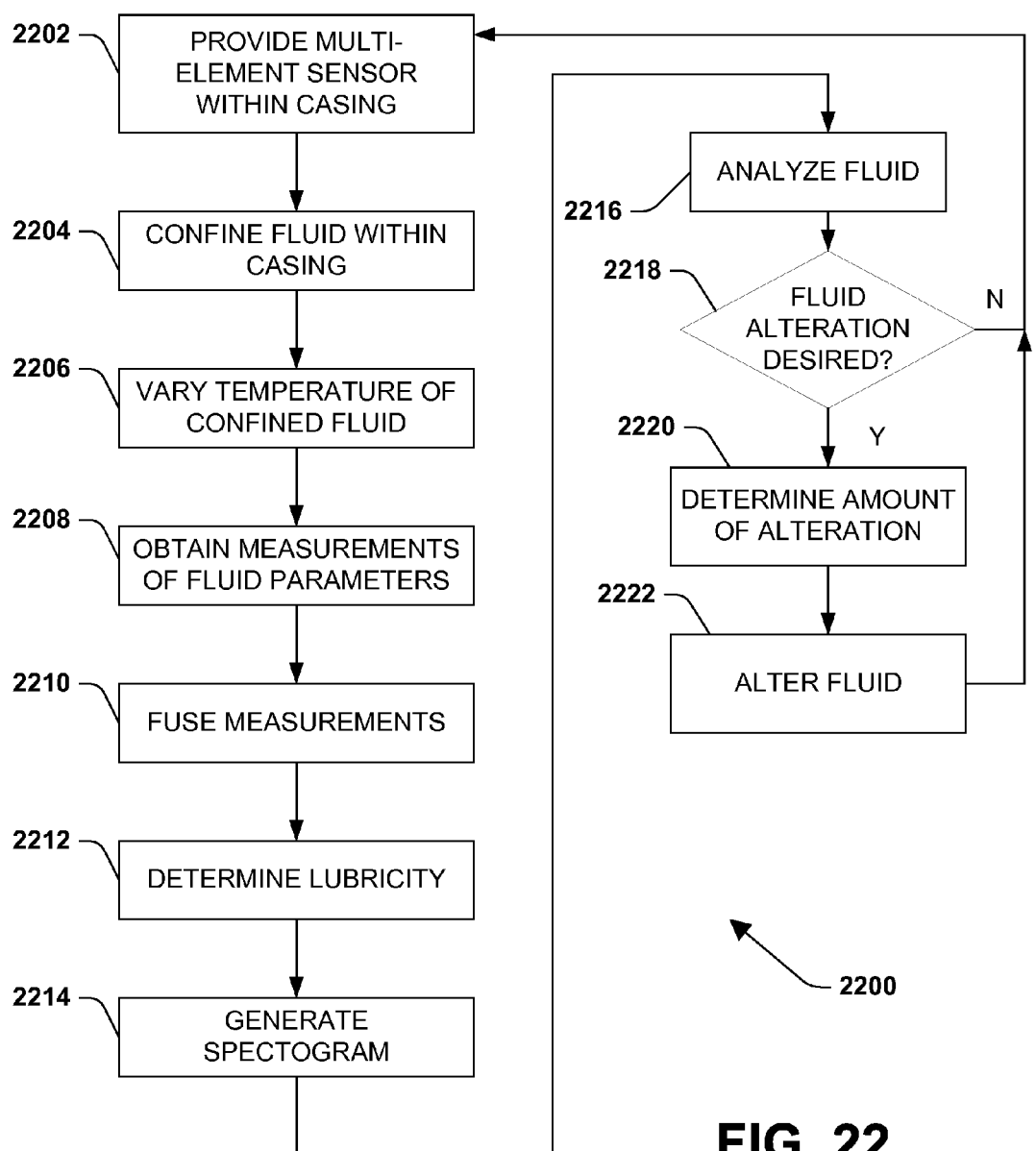
FIG. 22 is an illustrative flow diagram illustrating a methodology for calculating lubricity of a fluid in accordance with one aspect of the present invention.

Turning now to FIG. 22, a methodology 2200 for determining the degree of lubricity of a fluid and/or an FTIR spectrum plot of a fluid is illustrated. At 2202, a multi-element sensor is provided within a casing, which can allow a sample of fluid into the casing and confinement of the sample within the casing. At 2204, fluid is confined within the casing. For example, the casing can comprise a plurality of apertures that can be opened and closed by actuator(s) and/or MEMs valves. When the apertures are opened, fluid can enter/exit the casing. Upon filling the casing with fluid, the apertures can be closed, thus confining the fluid within the casing.

At 2206, temperature of the confined fluid is varied, which provides for a more complete and accurate mapping of readings from sensor elements to a FTIR spectrum. Moreover, alterations in lubricity with respect to alterations in fluid temperature can be monitored and utilized in connection with automatically maintaining fluid. At 2208, measurements of various parameters of a fluid are obtained. For example, temperature, pH, TAN, water, viscosity, density, etc. can all be monitored by sensor elements within the casing. At 2210, data from the sensor elements is filtered and/or fused. In accordance with one aspect of the present invention, one or more artificial neural networks are employed in connection with filtering and/or fusing data obtained by the sensor elements. At 2212, a measurement of lubricity of the fluid is determined based at least in part upon measured parameters. At 2214, a FTIR spectrum plot can be generated upon filtering and/or fusion of data obtained by the sensor elements. The lubricity measurement and FTIR spectrum plot can thereafter be employed in connection with automatically maintaining the fluid.

At 2216, the fluid is analyzed. For example, measurements obtained by sensing elements, a degree of lubricity of the fluid, and/or the FTIR spectrum plot can be utilized in connection with analyzing the fluid. At 2218 a determination is made regarding whether alteration of the fluid is desirable in connection with maintaining the fluid. For instance, an artificial neural network (or other suitable analysis network) can be employed to determine whether fluid alteration (e.g., chemical composition alteration) is desirable. If no change is desirable, the methodology 2200 can be repeated. If alteration of the fluid is desirable, at 2220 an amount of alteration is defined (e.g., an analysis component can be employed to determine amount of desirable alteration). At 2222, fluid alteration is effectuated. For instance, a controller can effectuate alteration of the fluid via relaying control commands to an additive reservoir. Thereafter the methodology 2200 can be repeated.

Figure 23:
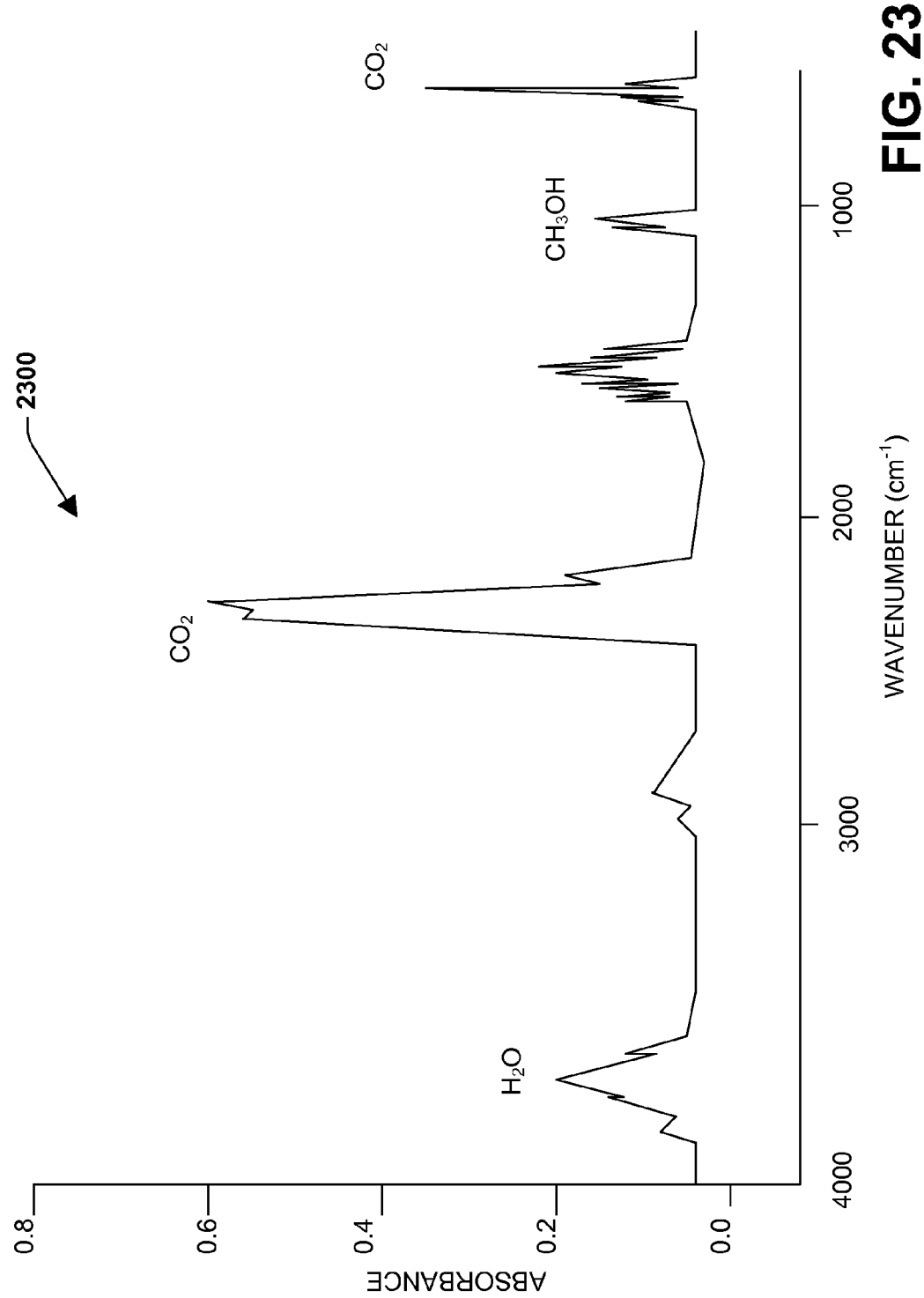
FIG. 23 is an exemplary Fourier Transform Infra Red spectrum plot in accordance with an aspect of the present invention.
Figure 24:
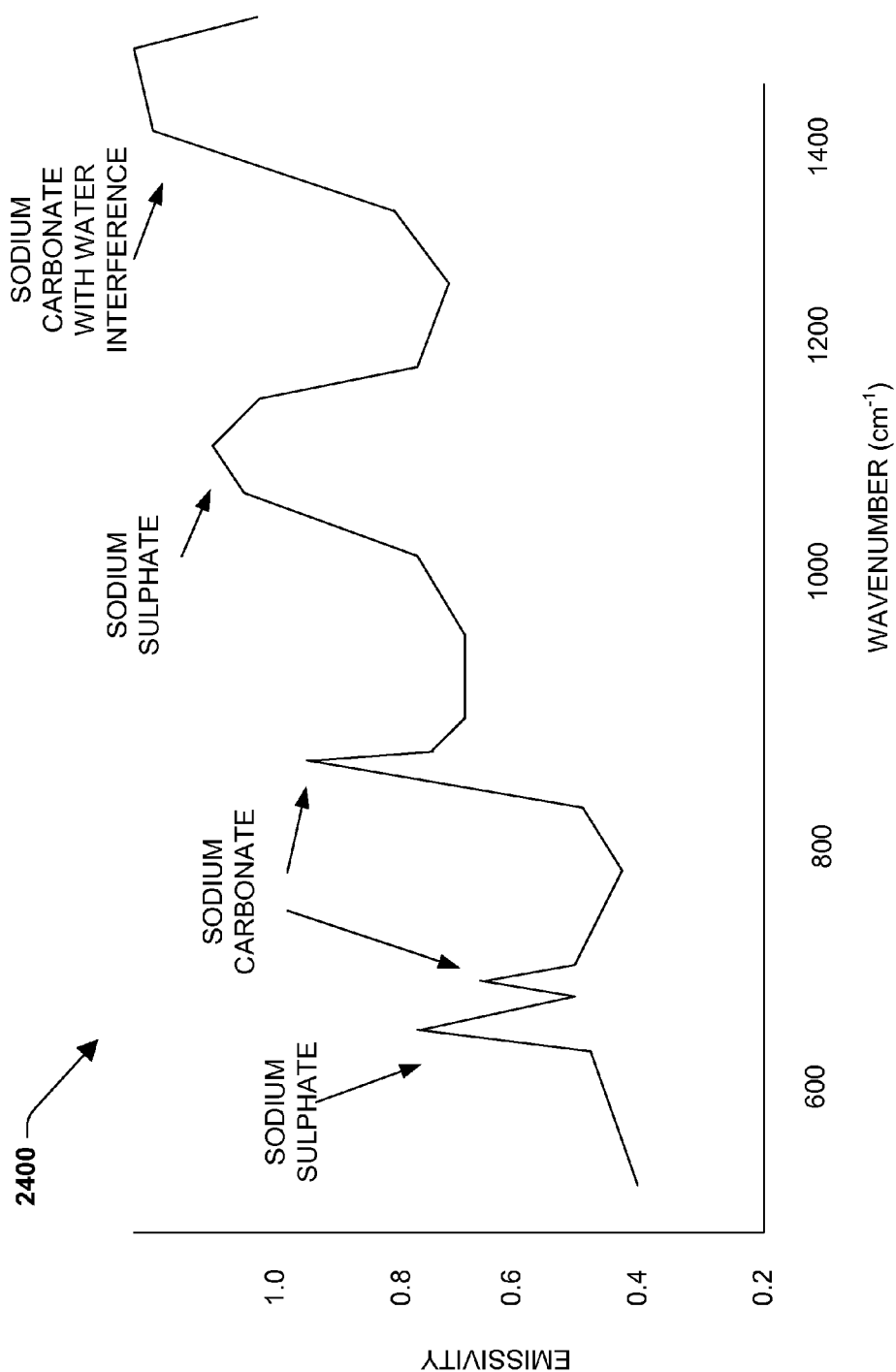
FIG. 24 is an exemplary Fourier Transform Infra Red spectrum plot in accordance with an aspect of the present invention.

Referring now to FIGS. 23 and 24, exemplary FTIR spectrum plots that can be synthesized via sensor element readings in accordance with an aspect of the present invention is illustrated. The FIGS. 23 and 24 illustrate that particular chemical compounds are indicated by peaks at particular wavenumbers. For example, referring to FIG. 23, the FTIR spectrum plot 2300 indicates a peak of carbon dioxide at wavenumbers of approximately 2400 and 250 cm$^{-1}$. Likewise, spectrum plot 2400 (FIG. 24) indicates a peak of sodium carbonate at wavenumbers of approximately 700 and 900 cm$^{-1}$. The present invention facilitates synthesizing a spectrum plot via sensing a plurality of parameters of a fluid.

Figure 25:
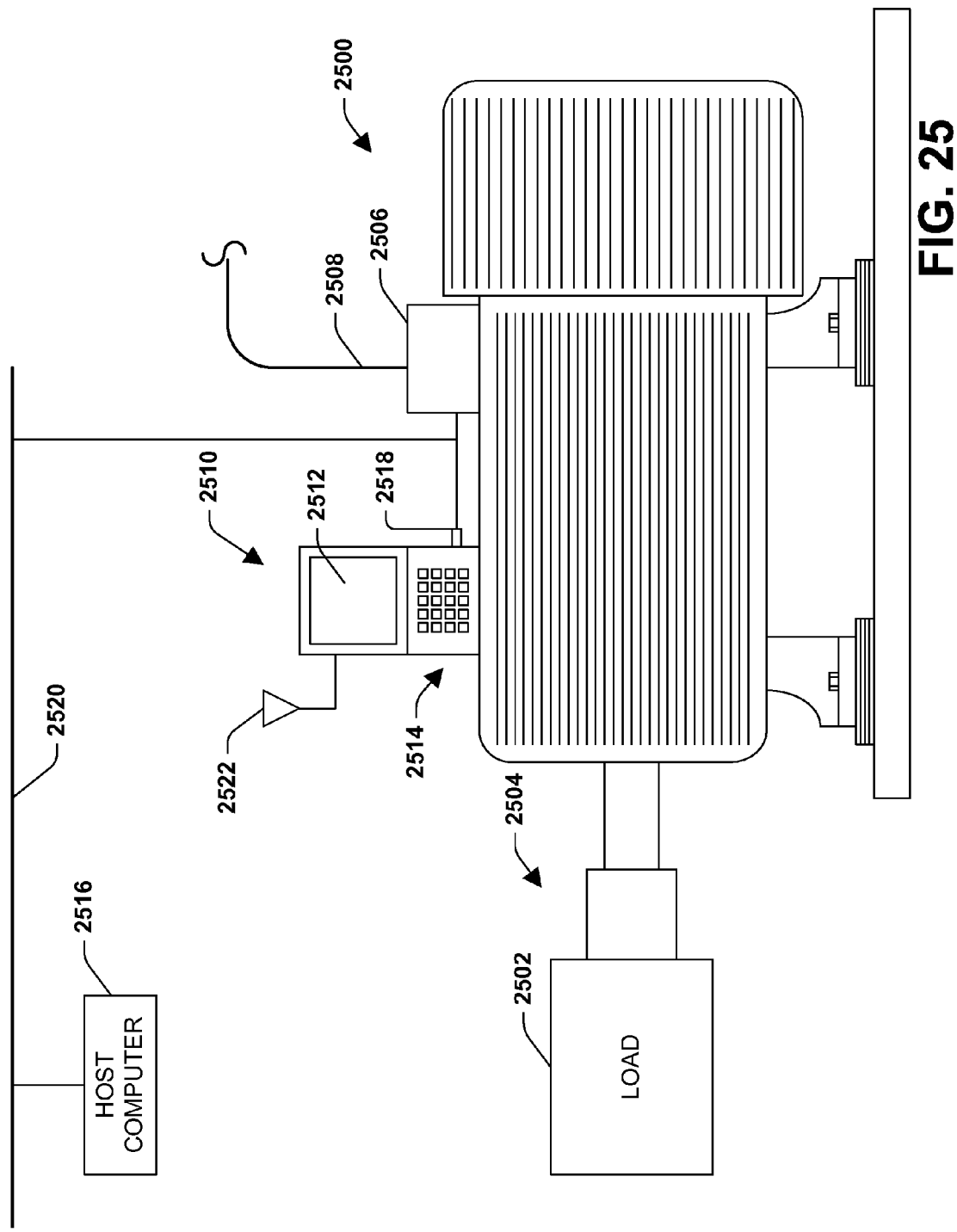
FIG. 25 is an exemplary environment in which the present invention can be employed.

In order to provide context for the present invention, FIG. 25 illustrates an exemplary environment in which the present invention may be employed. A three-phase AC induction motor 2500 is depicted driving a load 2502 through a shaft coupling 2504. The motor 2500 includes a junction box 2506 for receiving conductors from power lines via a conduit 2508, which are tied to power supply lines (not shown) of the motor 2500. The motor 2500 is AC powered and operates at an AC power line frequency of 60 Hz. However, it is appreciated that different line frequencies (e.g., 50 Hz) may be employed. Coupled to the motor 2500 is a fluid analyzer 2510 which as will be discussed in greater detail below provides for receiving and processing data relating to the health of fluid employed by the motor 2500.

The fluid analyzer 2510 includes a display 2512 for displaying to an operator information relating to the health of the fluid. It is to be appreciated that the fluid analyzer 2510 may also perform other functions relating to determining the health of the motor 2500 (e.g., current signature analysis, vibration analysis, etc.). The fluid analyzer 2510 further includes an operator input device 2514 in the form of a key pad which enables a user to enter data, information, function commands, etc. as is conventional. For example, the user may input information relating to fluid type via the keypad 2514 for subsequent transmission to a host computer 2516. In addition, the keypad 2514 may include up and down cursor keys for controlling a cursor that may be shown on the display 2512. The fluid analyzer 2510 includes a communications port 2518 for interfacing the fluid analyzer 2510 with the fluid sensor 1600 (FIG. 16) and the host computer 2516 via a suitable communications link.

In order to provide context for the present invention, FIG. 25 illustrates an exemplary environment in which the present invention may be employed. A three-phase AC induction motor 2500 is depicted driving a load 2502 through a shaft coupling 2504. The motor 2500 includes a junction box 2506 for receiving conductors from power lines via a conduit 2508, which are tied to power supply lines (not shown) of the motor 2500. The motor 2500 is AC powered and operates at an AC power line frequency of 60 Hz. However, it is appreciated that different line frequencies (e.g., 50 Hz) may be employed. Coupled to the motor 2500 is a fluid analyzer 2510 which as will be discussed in greater detail below provides for receiving and processing data relating to the health of fluid employed by the motor 2500.

Figure 26:
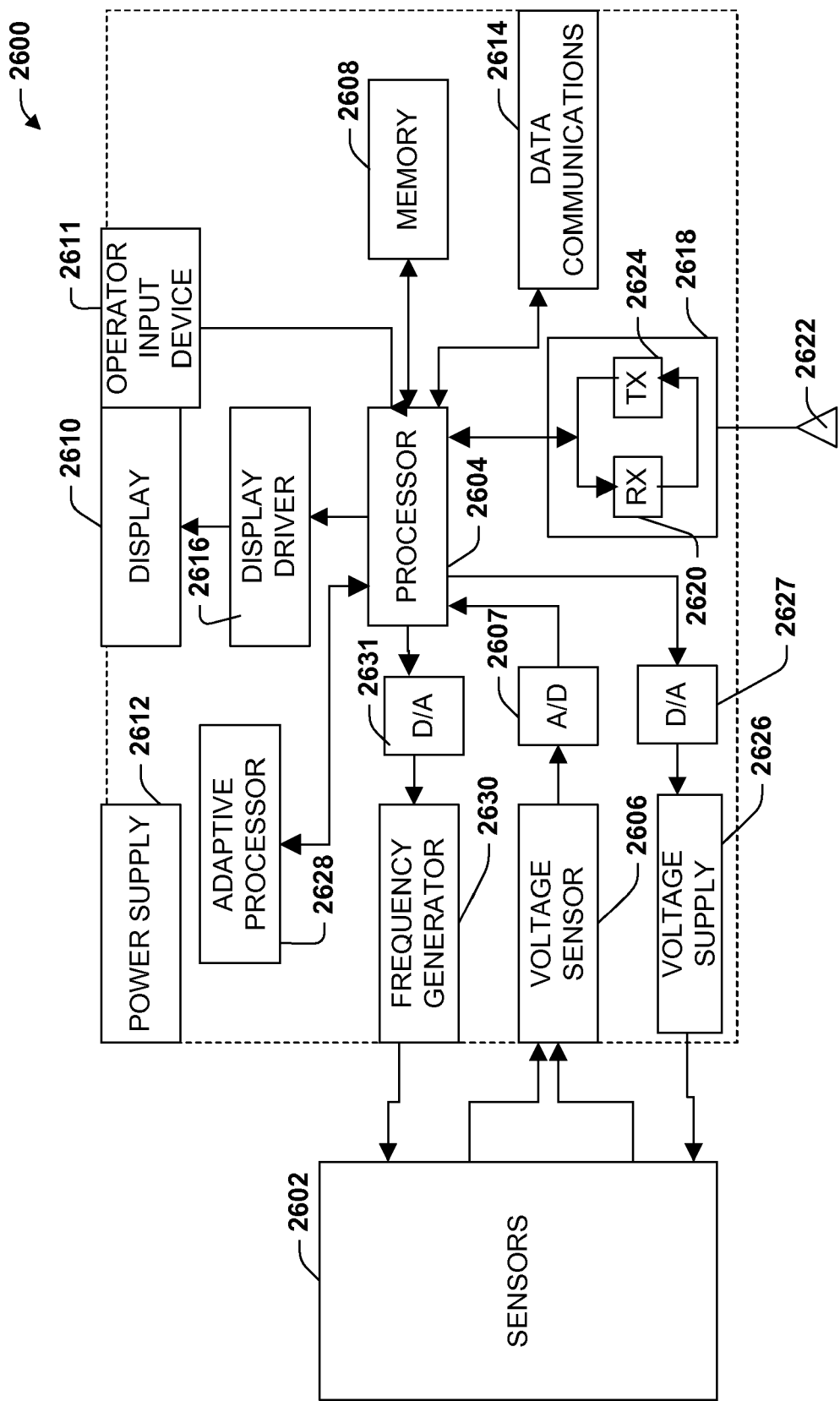
FIG. 26 is an exemplary schematic in accordance with one aspect of the present invention.

Referring now in to FIG. 26, a schematic representation of the present invention is shown according to one particular aspect of the present invention, wherein a fluid analyzer 2600 is integrated with the lubrication sensor 2602. However, it will be appreciated from the discussion herein that the lubrication analyzer 2600 may be located remotely from the motor 2500 (FIG. 25). Furthermore, it is to be appreciated that the host computer may serve to carry out substantially all of the functions described herein performed by the lubrication analyzer 2600. It is also to be appreciated that in accordance with another specific aspect of the present invention, the lubrication analyzer 2600 (absent certain components) may be integrated onto a semiconductor chip with the lubrication sensor 2602. In accordance with another specific embodiment, the lubrication analyzer 2600 may be completely integrated within the motor 2500 (e.g., in an intelligent motor), a gearbox, pump, filter, drain, or a bearing, for example.

According to an embodiment of the present invention, the lubrication analyzer 2510 is part of a communication system including a network backbone 2520. The network backbone 2520 may be a hardwired data communication path made of twisted pair cable, shielded coaxial cable or fiber optic cable, for example, or may be wireless or partially wireless in nature. Thus, the fluid analyzer 2510 can be provided with a wireless receiver/transmitter 2522 for receiving and/or relaying data pertinent to fluid analysis. Information can also be transmitted via the network backbone 2520 between the host computer 2516 and the lubrication analyzer 2510. The communication link preferably adheres to the RS232C or DeviceNet standard for communicating command and parameter information. However, any communication link suitable for carrying out the present invention may be employed. Note that the sensor, electronics, software, analysis, and communications may be embedded in the sensor device.

According to an embodiment of the present invention, the lubrication analyzer 2510 is part of a communication system including a network backbone 2520. The network backbone 2520 may be a hardwired data communication path made of twisted pair cable, shielded coaxial cable or fiber optic cable, for example, or may be wireless or partially wireless in nature. Thus, the fluid analyzer 2510 can be provided with a wireless receiver/transmitter 2522 for receiving and/or relaying data pertinent to fluid analysis. Information can also be transmitted via the network backbone 2520 between the host computer 2516 and the lubrication analyzer 2510. The communication link preferably adheres to the RS232C or DeviceNet standard for communicating command and parameter information. However, any communication link suitable for carrying out the present invention may be employed. Note that the sensor, electronics, software, analysis, and communications may be embedded in the sensor device. A more detailed discussion relating to the analytic relationship between fluid viscosity and fluid temperature is presented in co-pending U.S. Pat. No. 6,023,961.

In the preferred embodiment, the lubrication analyzer 2600 includes a housing that is suitably shielded to protect the lubrication analyzer 2600 from whatever environment (e.g., dust, moisture, heat, vibration, lubrication) the motor 2500 is working in. Additionally, the interior of the lubrication analyzer 2600 may be suitably insulated with thermal insulation between the motor and the lubrication analyzer so as to protect it from heat generated by the motor 2500. The lubrication sensor 2602 can include a pH sensor, an electrochemical sensor, a corrosion sensor, a conductivity sensor, a temperature sensor, a viscosity sensor, ferrous contaminant sensor, and any other suitable sensor that can be employed to measure various parameters of a fluid within a machine. The fluid sensor 2602 is operatively coupled to a processor 2604 of the lubrication analyzer 2600 via respective analog to digital (A/D) converters 2607 which convert the analog signals output from the fluid sensor 2602 to digital form for processing by the processor 2604.

A memory 2608 operatively coupled to the processor 2604 is also included in the fluid analyzer 2600 and serves to store program code executed by the processor 2604 for carrying out operating functions of the fluid analyzer 2600 as described herein. The memory 2608 also serves as a storage medium for storing information such as nominal fluid temperature, pH, electrochemistry, viscosity data, etc. The memory 2608 may also include machine specific data and acceptable error bounds/deviation values which may be used to facilitate determining the suitability of the fluid being analyzed. Furthermore, the memory 2608 may be used to store current and historical fluid or fluid parameter data, and corrective action which may be recommended. The data can be transmitted to a central processor and/or employed to perform time-based trending and analysis to determine fluid or fluid health and future health and desirable re-lubrication interval.

The memory 2608 includes read only memory (ROM) and random access memory (RAM). The ROM contains among other code the Basic Input-Output System (BIOS) that controls the basic hardware operations of the fluid analyzer 2600. The RAM is the main memory into which the operating system and application programs are loaded. The memory 2608 is adapted to store a complete set of the information to be displayed. According to a preferred embodiment, the memory 2608 has sufficient capacity to store multiple sets of information, and the processor 2604 could include a program for alternating or cycling between various sets of display information. This feature enables a display 2610 to show a variety of effects conducive for quickly conveying fluid state information to a user. Power is provided to the processor 2604 and other components forming the fluid analyzer 2600 from a power supply 2612.

The fluid analyzer 2600 includes a data communication system which includes a data communication port 2614 and communications card (not shown), which is employed to interface the processor 2604 with the host computer 2516 via the network 2520 (FIG. 25). The communication link preferably adheres to the RS232C or DeviceNet standard for communicating command and parameter information. However, any communication link suitable for carrying out the present invention may be employed.

A memory 2608 operatively coupled to the processor 2604 is also included in the fluid analyzer 2600 and serves to store program code executed by the processor 2604 for carrying out operating functions of the fluid analyzer 2600 as described herein. The memory 2608 also serves as a storage medium for storing information, such as nominal fluid temperature, pH, electrochemistry, viscosity data, etc. The memory 2608 may also include machine specific data and acceptable error bounds/deviation values which may be used to facilitate determining the suitability of the fluid being analyzed. Furthermore, the memory 2608 may be used to store current and historical fluid or fluid parameter data, and corrective action which may be recommended. The data can be transmitted to a central processor and/or employed to perform time-based trending and analysis to determine fluid or fluid health and future health and desirable re-lubrication interval.

The display 2610 is coupled to the processor 2604 via a display driver circuit 2616 as is conventional. The display 2610 may be a liquid crystal display (LCD) or the like. In one particular embodiment, the display 2610 is a fine pitch liquid crystal display operated as a standard CGA display. The display 2610 functions to display data or other information relating to the state of the fluid and if desired the state of the motor 2500 and recommend action (e.g. change lube in 2 weeks). For example, the display 2610 may display a set of discrete fluid or fluid condition indicia such as, for example, temperature, pH, electrochemistry, viscosity, and normal operation indicia which is displayed to the operator and may be transmitted over the network 2520. The display 2610 is capable of displaying both alphanumeric and graphical characters. Alternatively, the display 2610 may comprise one or more light emitting diodes (LEDs) (e.g., a tri-state LED displaying green, yellow or red colors depending on the health state of the fluid). An operator input device 2615 can be provided to allow an operator to communicate with the processor 2604 via the display 2610.

The fluid analyzer 2600 may also include its own RF section 2618 connected to the processor 2604. The RF section 2618 includes an RF receiver 2620 which receives RF transmissions from the host computer 2516 for example via an antenna 2622 and demodulates the signal to obtain digital information modulated therein. The RF section 2618 also includes an RF transmitter 2624 for transmitting information via a wireless link to the host computer 2516 for example in response to an operator input. This wireless link may eliminate the cost, noise problems and other problems related with the wireline link 2520. The RF section 2618 also permits multiple fluid analyzers to share information and to collaborate on multi-sensor data analysis or to collaborate and perform machinery, sub-system, or process diagnostics.

It should be appreciated that the present invention may be used in a system which does not include the host computer 2516. All processing, including data analyses and fluid or fluid state estimation and health determination could be accomplished by the processor 2604 and the results transmitted to a PC or a control computer, such as a programmable logic controller (PLC) (not shown), or only displayed locally on the fluid analyzer display screen 2610. Furthermore, only one data link may be required. According to another embodiment, the processor 2604 could be employed to simply trigger a single bit, digital output, which may be used to open a relay and turn the motor 2500 (FIG. 25) off or signal an alarm.

The display 2610 is coupled to the processor 2604 via a display driver circuit 2616 as is conventional. The display 2610 may be a liquid crystal display (LCD) or the like. In one particular embodiment, the display 2610 is a fine pitch liquid crystal display operated as a standard CGA display. The display 2610 functions to display data or other information relating to the state of the fluid and if desired the state of the motor 2500 and recommend actions (e.g. change lube in two weeks). For example, the display 2610 may display a set of discrete fluid or fluid condition indicia such as, for example, temperature, pH, electrochemistry, viscosity, and normal operation indicia which is displayed to the operator and may be transmitted over the network 2520. The display 2610 is capable of displaying both alphanumeric and graphical characters. Alternatively, the display 2610 may comprise one or more light emitting diodes (LEDs) (e.g., a tri-state LED displaying green, yellow or red colors depending on the health state of the fluid). An operator input device 2615 can be provided to allow an operator to communicate with the processor 2604 via the display 2610.

Once the processor 2604 has processed all of the respective fluid data, the processed data may be sent to the host computer 2516 for subsequent analysis and trending. The host computer 2516 may then make determinations as to the health of the fluid, the health of the machinery, the health of the process, or the health of the sensor elements based on the data received from the fluid analyzer 2600. The processor 2604 may perform data fusion of the various sensed fluid or fluid sensed parameter data to facilitate condensing, combining, evaluating and interpreting the various sensed data. Accordingly, fluid maintenance and automatic control for fluid alteration (e.g. additive release) can be scheduled to correspond with the state of the fluid. Additionally, the processed data can be compiled for trend analysis and forecasting. Since the fluid analyzer 2600 is integrated with the motor 2500, the data sampling rate can be substantially high thus providing for improved highly accurate and up to date data relating to the health of the fluid. However, as mentioned above, it is to be appreciated that fluid diagnosis, trend analysis, forecasting, etc. that could be performed by the host computer 2516 may also be performed directly by the fluid analyzer 2600.

The fluid analyzer 2600 includes a voltage supply 2626 which is operatively coupled to the processor 2604 and the fluid sensor 2602 via a D/A converter 2627. The voltage driver 2626 provides a series of desired voltage to the fluid sensor 2602 in order to drive certain sensing devices (e.g., an electrochemical sensor). The fluid analyzer can also comprise a frequency generator 2630 which communicates with the processor 2604 via a D/A converter 2631 if a voltage at particular frequencies or waveforms are required for proper operation of the sensor(s) 2602. The fluid analyzer 2600 may also include an adaptive processor 2628, such as, for example, a neural network and/or an expert system, to facilitate analyzing the health state of the fluid. Alternatively, the adaptive processor 2628 may be located in the host computer 2516 if desired. The programming or training of neural networks involves supplying the input and corresponding output data of samples containing features, similar to those being searched for. The neural network in turn learns by adjusting weights assigned to each of the neurons. The weights and threshold values of neurons of the neural network determine the propagation of data through the network and thus provide a desired output based on a respective set of inputs.

What is claimed is:

1. A system that facilitates in situ determination of lubricity in a fluid, comprising:
    a multi-element sensor positioned within a machine, the multi-element sensor obtains data regarding a plurality of parameters of a fluid, the multi-element sensor comprising two surfaces, at least one of the surfaces comprises a layer of material that wears readily;
    a component that measures capacitance resulting from wear of the material; and
    a component that calculates lubricity of the fluid based at least in part upon the measured parameters.

2. The system of claim 1, the multi-element sensor comprising:
    a first surface and at least a second surface with the fluid between the two surfaces, a first force is applied to the first surface and a second force is applied to the second surface causing the first and second surfaces to generate a frictional force between the two surfaces transmitted through the fluid; and
    a component that measures displacement relative to the two surfaces and the force causing the displacement.

3. The system of claim 2, at least one of the forces is substantially perpendicular to at least one other force.

4. The system of claim 2, at least one of the surfaces comprises a piezoelectric actuator beam.

5. The system of claim 2, further comprising at least one control component that controls the position of at least one of the first surface or the second surface.

6. The system of claim 5, further comprising at least one actuator that moves the first surface relative to the second surface, the at least one control component measures the force required to maintain the second surface fixed relative to the first surface, the force required is then used to calculate lubricity of the fluid.

7. The system of claim 1, further comprising a sensor fusion component that generates a Fourier Infra Red spectrum plot at least in part from measurements obtained from the multi-element sensor.

8. The system of claim 1, the multi-element sensor comprising:
    a rotating disk;
    a surface that tangentially contacts the rotating disk; and
    a component that monitors a force required to rotate the disk a particular distance.

9. The system of claim 1, wherein the component that calculates the lubricity of the fluid comprises one or more artificial neural networks.

10. The system of claim 1, wherein the component that calculates the lubricity of the fluid comprises at least one of a support vector machine, an expert system, a Bayesian belief network, a fuzzy logic algorithm, and a data fusion engine.

11. The system of claim 1, the component automatically adjusts chemical composition of the fluid based at least in part upon the calculated lubricity.

12. The system of claim 1, further comprising a control component that controls operation of a machine based at least in part on the calculated lubricity.

13. A method for in situ determination of lubricity in a fluid within machinery, comprising:
    placing two surfaces together with fluid between the two surfaces;
    moving one surface to generate a frictional force by relative movement between the two surfaces and the fluid; and
    calculating the force required to prevent the other surface from moving relatively and using the information for lubricity measurement.

14. The method of claim 13, further comprising: fusing data relating to forces utilized to generate the frictional force and relative displacement of the two surfaces with friction force data to determine lubricity in the fluid.

15. The method of claim 13, the frictional force is generated by applying at least one force that is substantially perpendicular to at least one other force.

16. The method of claim 13, further comprising passing fluid between the two surfaces while the two surfaces are held in a fixed position relative to one another.

17. A system for calculating lubricity of a fluid, comprising:
    means for exerting a force on at least two surfaces to create a friction force between the two surfaces;
    means for maintaining fluid between the two surfaces;
    means for monitoring the force exerted on the surfaces; and
    means for calculating the lubricity of the fluid from the forces.

18. The system of claim 17, the two surfaces are moved relative to one another to create the friction force.

* * * * *